US007989175B2

(12) United States Patent
Moreau

(10) Patent No.: US 7,989,175 B2
(45) Date of Patent: Aug. 2, 2011

(54) METHOD OF CLASSIFYING HUMAN SUBJECTS HAVING ADOLESCENT IDIOPATHIC SCOLIOSIS

(75) Inventor: Alain Moreau, Montreal (CA)

(73) Assignee: Hôpital Sainte-Justine, Montreal (CA)

( * ) Notice: Subject to any disclaimer, the term of this patent is extended or adjusted under 35 U.S.C. 154(b) by 288 days.

(21) Appl. No.: 12/232,141

(22) Filed: Sep. 11, 2008

(65) Prior Publication Data

US 2009/0111110 A1    Apr. 30, 2009

Related U.S. Application Data

(63) Continuation of application No. 10/505,951, filed as application No. PCT/CA03/00286 on Feb. 28, 2003, now abandoned.

(30) Foreign Application Priority Data

Feb. 28, 2002   (CA) ...................................... 2373854

(51) Int. Cl.
*G01N 33/567* (2006.01)
(52) U.S. Cl. ...................................... 435/7.21
(58) Field of Classification Search ........................ None
See application file for complete search history.

(56) References Cited

FOREIGN PATENT DOCUMENTS

| EP | 0 892 046 | 1/1999 |
|---|---|---|
| WO | WO 95 35320 | 12/1995 |
| WO | WO 98 03549 | 1/1998 |
| WO | WO 01 09383 | 2/2001 |
| WO | WO 03 073102 | 9/2003 |

OTHER PUBLICATIONS

Axenovich et al. "Segregation analysis of idiopathic scoliosis: demonstration of a major gene effect", (1999), Am J Med Genet;, vol. 86(4):389-394.
Bagnall et al., "The effects of melatonin therapy on the development of scoliosis after pinealectomy in the chicken", (1999), J Bone Joint Surg Am, vol. 81(2):191-199.
Bagnall et al. "Melatonin levels in idiopathic scoliosis. Diurnal and nocturnal serum melatonin levels in girls with adolescent . . . "(1996), Spine; vol. 21(17): 1974-1978.
Bagnall et al., "Pineal transplantation after pinealectomy in young chicken has no effect on the development of scoliosis", (2001) Spine, vol. 26, No. 9: 1022-1027.
Beuerlein et al., "Development of Scoliosis Following Pinealectomy in Young Chickens Is Not the Results of . . . " (2001), Microscopy Research and Technique, vol. 53: 81-86.
Blank et al., "A genomic approach to scoliosis pathogenesis", (1999), Lupus; vol. 8(5):356-360.
Borjigin et al., "The pineal gland and melatonin: molecular and pharmacologic regulation", (1999), Annu Rev Pharmacol Toxicol; vol. 39:53-65.

Brodner et al., "Melatonin and adolescent idiopathic scoliosis". (2000), J Bone Joint Surg Br; vol. 82(3):399-403.
Bruls et al., "Melatonin. I. Physiology of its secretion", (2000) Rev. Med. Leige, vol. 55, No. 8: 785-792, (Abstract).
Cardinali et al., "Melatonin site and mechanism of action: single or multiple?", (1997), J Pineal Res; vol. 23(1):32-39.
Cheng et al., Persistent osteopenia in adolescent idiopathic scoliosis. A longitudinal follow up study, (1999), Spine, vol. 24(12):1218-1222.
Cheng et al., "Osteopenia in adolescent idiopathic scoliosis: a histomorphometric study", (2001), Spine; vol. 26(3):E19-E23.
Cheung et al., "Effect of Melatonin Suppression on Scoliosis Development in Chickens . . . ", (2003), Spine vol. 28, No. 17 pp. 1941-1944.
Cheung et al., "The Effect of Pinealectomy on Scoliosis Development in Young Nonhuman Primates", (2005), Spine vol. 30, No. 18 pp. 2009-2013.
Connor et al., "Genetic aspects of early childhood scoliosis", (1987), Am J Med Genet; vol. 27(2):419-424.
Conway et al, "Chimeric melatonin mt1 and melatonin-related receptors: Identification of domains and residues . . . ", Journal of Biol. Chem., vol. 275, No. 27: 20602-20609.
Courtois et al., "Bone mineral density at the femur and lumbar spine in a population of young women treated for scoliosis . . . ", (1999), Rev Rhum Engl Ed, vol. 66(12):705-710.
Cowburn et al., "Preservation of Gi-protein inhibited adenylyl cyclase activity in the brains of patients with Alzheimer's disease", (1992), Neurosci Lett; 141(1):16-20.
De Georges et al., "Idiopathic Scoliosis: Genetic and Enrironmental Aspects", (1967), J. med. Genet., vol. 4: 251-257.
Drazen et al. , "Melatonin enhancement of splenocyte proliferation is attenuated . . . ",(2001) Am. J. Physiol. Regulatory Integrative Comp Physiol., vol. 280 pp. R1476-R1482.
Fagan et al., Total 24-Hour Melatonin Secretion in Adolescent Idiopathic Scoliosis: A Case-Control Study, (1998), Spine vol. 23, No. 1 pp. 41-46.
Feldman RD. "Insulin-mediated sensitization of adenylyl cyclase activation", (1993), Br J Pharmacol; vol. 110(4):1640-1644.
Garcia-Perganeda et al., "Signal Transduction for Melatonin in Human Lymphocytes", The Journal of Immunology, vol. 159 (1997) pp. 3774-3781.
Giampietro et al. "Synteny-defined candidate genes for congenital and idiopathic scoliosis", (1999), Am J Med Genet; 83(3):164-177.
Hans et al., "No diffuse osteoporosis in lumbar scoliosis but lower femoral bone density on the convexity", (1996), Bone; vol. 18(1):15-17.
Hilibrand et al., "The Role of Melatonin in the Pathogenesis of Adolescent Idiopathic Scoliosis", (1996), Spine vol. 21, No. 10, pp. 1140-1146.
Hyatt et al., "Initiation of vertebrate left-right axis formation by maternal Vg1", (1996), Nature, vol. 384:62-65.
Iuvone et al., "Melatonin Receptor-Medicated Inhibition of Cyclic AMP Accumulation in Chick Retinal Cell Cultures", (1994), Journal of Neurochemistry, vol. 63, No. 1: 118-124.
Jockers et al., "Structure and function of melatonin receptors", (1998), C R Soc Biol., vol. 192(4):659-667.

(Continued)

*Primary Examiner* — Rebecca Prouty
*Assistant Examiner* — Paul Martin
(74) *Attorney, Agent, or Firm* — Goudreau Gage Dubuc; Julie Gauvreau

(57) ABSTRACT

A method for classifying human subjects having adolescent idiopathic scoliosis (AIS) into AIS subgroups, comprising detecting an impairment in the melatonin-signaling pathway in a cell sample from the subject, wherein the impairment is detected by an accumulation of cyclic adenosine 5'-monophosphate (cAMP) in the cell sample as compared to a control sample in the presence of a known melatonin-signaling pathway agonist, wherein the results of the detection step enable the classification of the subject having AIS into an AIS subgroup.

9 Claims, 21 Drawing Sheets

OTHER PUBLICATIONS

Kaziro et al., "Structure and function of signal-transducing GTP-binding proteins", (1991) Annu Rev Biochem, vol. 60:349-400.

Kennaway, D. J., "Melatonin and development: Physiology and Pharmacology", (2000) Seminars in Perinatology, vol. 24, No. 4: 258-266.

Machida et al., "Pathogenesis of idiopathic scoliosis. Experimental study in rats", (1999), Spine; vol. 24(19):1985-1989.

McCarrey et al., "Genetics of scoliosis in chickens", (1981), J Hered, vol. 72 (1):6-10.

Nakade et al., "Melatonin stimulates proliferation and type I collagen synthesis in human bone cells in vitro" (1999), J Pineal Res; vol. 27(2):106-110.

O'Kelly et al., The Production of Scoliosis After Pinealectomy in Young Chickens, Rats, and Hamsters, (1999), Spine vol. 24, No. 1, pp. 35-43.

Papaioannou et al., "G-protein signaling pathways and oestrogen: a role of balanced maintenance in osteoblasts". (1999) Biochim Biophys Acta; vol. 1449(3): 284-292.

Purkiss et al., "Idiopathic Scoliosis in Families of Children With Congenital Scoliosis", (2002), Clin Orthop Relat Res No. 401, pp. 27-31.

Roka et al., "Tight association of the human Mel(1a)-melatonin receptor and G(i): precoupling and constitutive activity", (1999), Mol Pharmacol, vol. 56(5):1014-1024.

Roth et al., "Melatonin promotes osteoblast differentiation and bone formation", (1999), J Biol Chem; vol. 274(31):22041-22047.

Sadat-Ali et al., Adolescent idiopathic scoliosis. Is low melatonin a cause?, (2000) Joint Bone Spine; 67(1):62-64.

Sjoblom et al., "Peripheral melatonin mediates neural stimulation of duodenal mucosal . . .", (2001), The Journal of Clinical Investigation, vol. 108, No. 4: 625-633.

Tintut et al., "Inhibition of osteoblast-specific transcription factor Cbfa1 by the cAMP pathway in osteoblastic cells . . .", (1999), J Biol Chem; vol. 274(41):28875-28879.

von Gall et al. "Transcription factor dynamics and neuroendocrine signaling in the mouse pineal gland . . .", (2000), Eur J Neurosci; vol. 12(3):964-972.

Wang et al., "Changes in serum melatonin levels in response to pinealectomy in the chicken and its correlation with . . . ", (1998), Spine; vol. 23(22):2377-2381.

Wise et al., "Localization of susceptibility to familial idiopathic scoliosis", (2000), Spine; vol. 25(18):2372-2380.

Whynne-Davies Ruth, "Familial (Idiopathic) Scoliosis", (1968), The Journal of Bone and Joint Surgery, vol. 50B, No. 1: 24-30.

METHOD OF CLASSIFYING HUMAN SUBJECTS HAVING ADOLESCENT IDIOPATHIC SCOLIOSIS

CROSS-REFERENCE TO RELATED APPLICATIONS

This application is a continuation application of U.S. patent application Ser. No. 10/505,951 filed Aug. 27, 2004 now abandoned, which is a National Entry Application of PCT application no PCT/CA2003/00286, filed on Feb. 28, 2003 and published in English under PCT Article 21(2), which itself claims priority on Canadian Patent Application 2,373,854, filed on Feb. 28, 2002. All documents above are incorporated herein in their entirety by reference.

FIELD OF THE INVENTION

The present invention relates to a method of diagnosing adolescent idiopathic scoliosis and related syndromes causing spinal deformities and a method for screening for a compound useful in the treatment of these diseases. More specifically, the present invention is concerned with a neuroendocrinal method of diagnosing adolescent idiopathic scoliosis and related syndromes causing spinal deformities and a method for screening for a compound useful in the treatment of these diseases.

BACKGROUND OF THE INVENTION

The etiology of adolescent idiopathic scoliosis (AIS), a disease affecting 0.2 to 6% of the population, is unclear. AIS affects mainly girls in number and severity but in spite of several studies suggesting a genetic predisposition, the form of inheritance remains uncertain (3; 4; 4-6). Several divergent perspectives have been postulated to better define this etiology (reviewed in (2; 21-23)). Genetics, growth hormone secretion, connective tissue structure, muscle structure, vestibular dysfunction, melatonin secretion, and platelet microstructure are major areas of focus. The current opinion is that there is a defect of central control or processing by the central nervous system (CNS) that affects a growing spine and that the spine's susceptibility to deformation varies from one individual to another.

CNS Hypothesis: B. Muscle Spindle Ontology and AIS

In 1999, Dubousset suggested that AIS is probably caused by a proprioception control problem, a neuromuscular disorder in relation with the neurotransmitter involved with the bipedal condition.

Muscles spindles are skeletal muscle sensory organs that provide axial and limb position information (proprioception) to the CNS. It has been proposed that muscle spindles act as muscle receptors involved in the detection of movement, both passive and active.(5) Spindles consist of encapsulated muscles fibers (intrafusal fibers) that are innervated by specialized motor and sensory axons. Indeed, histologic and histochemical analysis of the distribution of muscle spindles in paraspinal musculature of patients suffering from AIS show few muscle spindles in the scoliotic muscle.(6) Although the mechanism involved in spindle ontogeny are poorly understood, the innervation of a subset of developing myotube (type I) by peripheral sensory afferents (group Ia) is a critical event for inducing intrafusal fiber differentiation and subsequent spindle formation. The inactivation of Egr3, a zing-finger transcription factor, by gene targeting generates mice exhibiting gait ataxia, increased frequency of perinatal mortality, scoliosis, resting tremors and ptosis. Egr3-deficient mice lacked muscles spindles, a finding that is consistent with their profound gait ataxia. Egr3 is highly expressed in developing muscle spindles, but not in Ia afferent neurons or their terminals during developmental periods that coincide with the induction of spindle morphogenesis by sensory afferent axons. This indicates that type I myotubes are dependent upon Egr3-mediated transcription for proper spindle development.(7-9) In addition, Rodgers et al., reported the detection of Pax7 expression, a member of the Pax family of transcription factor, in the capsules surrounding adult mouse muscle spindles where it may be implicated in the formation and maintenance of neuromuscular contacts within the muscle spindles throughout life.(10) The recent report of Ichikawa et al.,(11) showing in muscle spindles the presence of OPN-immunoreactive spiral axon terminals suggest that OPN could behave as a molecular mechanoreceptor within the spindles. This aspect is further supported from the fact that OPN-null mice, which are normal and viable, are not responding to biomechanical stimuli.

Neuroendocrine Hypothesis

Recent experiments involving pinealectomy in chicken and more recently in rats maintained in a bipedal mode led to an alternate hypothesis. These surgeries produced a scoliosis (7; 8; 8-10) resembling in many aspects the human disease and pointed to a neuroendocrine hypothesis involving a melatonin deficiency as the source for AIS. Treatment after pinealectomy in both animal models with melatonin, the major hormone of the pineal gland, prevented the formation of scoliosis (11).

The biological relevance of melatonin in AIS remains controversial however since no significant decrease in circulating melatonin level has been observed in a majority of studies (12; 13; 13; 14).

There is therefore a need for a useful method for diagnosing AIS and other diseases involving spinal deformities and for identifying compounds for treating these diseases.

SUMMARY OF THE INVENTION

The present invention demonstrates for the first time that AIS patients exhibit a melatonin-signaling pathway impairment and that this impairment can be observed through various manifestations.

In particular, the present invention demonstrates for the first time a dysfunction of melatonin-signaling in bone-forming, muscle-forming cells and blood cells of AIS patients. In addition, the present invention demonstrates for the first time that non-functional Gi proteins normally coupled to melatonin receptors MT1 and MT2 is related to such dysfunction.

More specifically, in accordance with the present invention, there is provided a method for diagnosing an increased risk for a disease characterized by a dysfunctional melatonin-signaling pathway in an animal, comprising detecting the presence or absence of at least one impairment in melatonin-signaling pathway in at least one of the animal's cells, wherein the presence of at least one impairment in melatonin-signaling pathway indicates that the animal possesses an increased risk of developing said adolescent idiopathic scoliosis or other disease.

The method of the present invention may also be advantageously used to diagnose a particular type of disease characterized by a dysfunctional melatonin-signaling pathway by determining whether the results of the assay correspond to those of a previously tested animal affected by this particular type of disease. For instance, it would be possible to determine with the method for diagnosing of the present invention, whether an animal is affected by AIS of group 1, 2 or 3 (as described in Table 2 below) by determining its osteoblast responsiveness to melatonin treatment. This is particularly interesting if the most effective drug for treating or preventing AIS varies between the groups (1, 2 or 3). The method for diagnosing of the present invention therefore permits a better selection of the drug to be used for a particular patient.

According to another embodiment of the present invention, there is also provided a method of screening for a compound useful in the treatment of a disease characterized by a dysfunctional melatonin-signaling pathway, said method comprising the steps of contacting a candidate compound with at least one cell expressing at least one melatonin-signaling pathway impairment in the presence of a known melatonin-signaling pathway agonist, wherein the candidate compound is selected if said melatonin-signaling pathway impairment is reduced in the presence of the candidate compound as compared to that in the absence thereof. This method can be used for screening for compounds able to modulate melatonin-signaling impairment generally. It can however also be used to determine which compound is the most effective for modulating and in particular reducing or counteracting the melatonin-pathway impairment in cells from a specific group of patient or for a specific patient. Indeed, the most effective compound for these purposes may vary from one patient to the next. The method of screening of the present invention may therefore be used to identify which compound is the most effective in counteracting the melatonin-signaling pathway impairment in a specific group of patients or in one patient in particular.

In a specific embodiment, said disease characterized by a dysfunctional melatonin-signaling pathway is adolescent idiopathic scoliosis or an other disease involving spinal deformities. In another specific embodiment, said disease characterized by a dysfunctional melatonin-signaling pathway is adolescent idiopathic scoliosis. In another specific embodiment, said impairment is detected by an accumulation of cyclique adenosine 5'-monophosphate (cAMP) in at least one of said cells. In another specific embodiment, said accumulation of cyclique adenosine 5'-monophosphate (cAMP) is induced by a known activator of adenylyl cyclase, and wherein the inhibition of said accumulation by a known melatonin-signaling pathway agonist is detectably reduced in at least one said cells as compared to that obtained in a control cell. In another specific embodiment, said known melatonin-signaling pathway agonist is melatonin or an analog thereof. In another specific embodiment, said known melatonin-signaling pathway agonist is GTP or an analog thereof. In another specific embodiment, said known activator of adenylyl cyclase is forskolin or an analog thereof. In another specific embodiment, said impairment is detected by an absence of proliferation of in at least one of said cells in presence of a known melatonin-signaling pathway agonist. In another specific embodiment, said impairment is detected by a reduction of inhibition of osteoclasts resorption activity by the known melatonin-signaling pathway agonist, and wherein the candidate compound is selected if said reduction of inhibition of osteoclasts resorption activity is inhibited in the presence of the candidate compound as compared to that in the absence thereof. In another specific embodiment, said cells are selected from the group consisting of osteoblasts, osteoclasts, lymphocytes, monocytes and myoblasts. In another specific embodiment, said cells are blood cells. In another specific embodiment, said cells are lymphocytes. In another specific embodiment, said impairment is detected by an accumulation of cyclique adenosine 5'-monophosphate (cAMP) in said cell as compared to that in a control cell. In another specific embodiment, the method further comprises the step of artificially inducing said accumulation of cyclique adenosine 5'-monophosphate (cAMP) by a known activator of adenylyl cyclase.

According to a further embodiment of the present invention, there is also provided a method of formulating a drug useful in the treatment of a disease characterized by a dysfunctional melatonin-signaling pathway, said method comprising the steps of contacting a candidate compound with at least one cell expressing at least one melatonin-signaling pathway impairment, wherein the candidate compound is selected if said melatonin-signaling pathway impairment is reduced in the presence of the candidate compound as compared to that in the absence thereof, and formulating said drug with said selected candidate compound.

The present invention discloses such compounds able to modulate melatonin-signaling pathway impairment including melatonin, forskolin and estradiol.

According to specific embodiments of the present invention, the disease characterized by a dysfunctional melatonin-signaling pathway is adolescent idiopathic scoliosis or another disease involving spinal deformities. More specifically, the impairment may be detected by an accumulation of cyclique adenosine 5'-monophosphate (cAMP) in a cell of the animal, an absence of said cells proliferation in presence of the known melatonin-signaling pathway agonist, and a reduction of inhibition of osteoclasts resorption activity induced by the known melatonin-signaling pathway agonist, wherein the candidate compound is selected if said reduction of inhibition of osteoclasts resorption activity is inhibited in the presence of the candidate compound as compared to that in the absence thereof. Note that any cell from tissues targeted by melatonin or expressing melatonin signalisation and wherein other pathway members do not mask melatonin-signaling impairments may be used in accordance with the methods of the present invention. The cells used herein were selected in part for their accessibility. Hence, cells such as osteoblasts, osteoclasts, lymphocytes, monocytes and myoblasts are advantageously accessible and may conveniently be used in the methods of the present invention. Blood cells in particular are particularly accessible and provide for a more rapid testing. In specific embodiment, said known melatonin-signaling pathway agonist is melatonin, GTP or analogs thereof. Any other known melatonin-signaling pathway agonist may be used in accordance with the present invention. In a specific embodiment, the known activator of adenylyl cyclase is forskolin.

Melatonin-Signaling Pathways

Melatonin-signaling pathways have been better characterized in the brain, the pituitary gland and few peripheral tissues than bone or other musculoskeletal tissues. Melatonin exerts its effects through specific, high-affinity receptors.(12-14) These melatonin receptors are coupled to guanine nucleotide-binding proteins (G proteins), and their activation leads to the inhibition of adenylyl cyclases, which are responsible for the accumulation of cyclic adenosine 5'-monophosphate (cAMP) (15). Through molecular cloning, three G protein-coupled melatonin receptor subtypes have been identified in vertebrates. The ligand-binding properties and signaling mechanisms of these receptors are remarkably similar. Each receptor subtypes is coupled to inhibition of cAMP accumulation. The MT1 (MelR1a) and MT2 (MelR1b) receptor genes are present in mammals and several lines of evidence demonstrated that MT1 is the receptor that mediates the reproductive and circadian responses to melatonin. The third receptor, MelR1c (two isoforms a and β) has been only detected in the chicken and in Xenopus. A second type of melatonin receptor called MT3 has been first discovered based on its pharmacological properties that are quite distinct from the MT1 and MT2 receptor subtypes. Recently, the human and mouse MT3 receptors have been cloned and correspond to protein encoded by the quinone reductase 2 gene (QR2).(16) The precise role of this gene in melatonin signal transduction remains to be determined. Besides the membranous receptors, the orphan nuclear receptors RZRα and β, have been proposed to interact with melatonin but such interaction remains elusive. Interestingly, estrogens markedly inhibit the expression and synthesis of G protein a-subunits (Gi1-3 and Gs) in osteoblast cultures suggesting that melatonin-signaling may be modulated by estrogens.(17) Furthermore, estrogens are able to increase calmodulin expression, independently of both estrogens receptors (ERα and β).(18) This is particularly interesting because calmodulin and melatonin exert a mutual antagonism,(19; 20) and membrane-bound calmodulin is able to interact with melatonin as demonstrated in Xenopus.(21) Moreover, melatonin has the property to destabilize the ERs DNA-binding on their cognate sequence. (22)

Fundamental Aspects of Melatonin Signal Transduction

Expression analysis revealed that melatonin up-regulates key osteoblasts terminal differentiation markers like osteocalcin (OC), osteopontin (OPN) and bone sialoprotein (BSP). This activation was already detectable after only 10 min of stimulation suggesting that melatonin stimulates osteoblast differentiation in vitro through specific interactions with one of its membranous receptors. It was then determined whether this transcriptional activation was mediated by MT1 or MT2 receptor subtype, and demonstrated that both receptor subtypes are expressed although time-course expression analysis revealed that MT2 receptor expression was predominantly detected. At the protein level, IHC experiments demonstrated the presence of both melatonin receptors at the cell surface. In parallel, co-immunoprecipitation assays with osteoblast purified membranes demonstrated for the first time a preferential pre-coupling of Gi proteins, Gi3>Gi2, to MT2 receptors in absence of ligand while in presence of melatonin both proteins binding were increased. Similar analysis with MT1 receptor revealed that only Gi3 was pre-coupled to this receptor. No interaction was detected between Gi1 proteins and both melatonin receptors.

Bone Mineral Density in Pinealectomized Chicken

Scoliotic and non-scoliotic pinealectomized chicken showed a similar and significant decrease in bone mineral density suggesting that bone tissue is indeed a target of melatonin action. EMG analysis performed with the same set of chicken showed a 75% increase in muscular tone of paraspinal muscles on both sides while a 60% asymmetrical increase of the muscular activity was measured on the left side, which correlated with the side of the scoliosis curve (99% left sided).

As used herein, the expression "melatonin-signaling pathway impairment" or "dysfunction" is meant to refer to any impairment in this pathway that characterizes cells from patients with AIS and related syndromes causing spinal deformities and includes but is not limited to: absence of inhibition of osteoclasts resorption activity, accumulation of cAMP in an animal cell, an hypofunctionality of Gi proteins, a phosphorylation state of Gi proteins distinct from that of normal cells, an absence of proliferation of certain cells in response to melatonin, a mutation in a gene encoding a member of the melatonin signaling pathway.

As used herein, the term "control cells" is used to refer to any cell not expressing the melatonin-signaling pathway of the cell under scrutiny. It includes cells from non-scoliotic animals and cells from animals displaying other types of scoliosis.

As used herein, the expression "analog thereof" is meant to include any compound displaying the same activity as that for which the compound of reference is used. For instance, Gpp (NH)p is an analog of GTP.

In a specific embodiment, the cAMP accumulation may have been artificially induced by a known adenylyl cyclase activator such as forskolin and inhibited by an melatonin-signaling pathway agonist such as melatonin itself or any agonist known for inhibiting cAMP accumulation such as GTP or Gpp(NH)p. An absence of cAMP accumulation by these known agonists is interpreted as a melatonin-signaling impairment of the subject cell and of the animal from which the cell was isolated.

As used herein, the methods for diagnosing AIS and related syndromes causing spinal deformities in an animal comprises detecting any melatonin-signaling pathway impairment in at least one of the animal cells such as but not limited to lymphocytes, monocytes, osteoclastes, osteoblasts, myoblasts from the animal, and according to specific embodiments the animal is a human.

Assays to Identify Peptides of the Present Invention

Preferred methods for testing the ability of candidate compounds to modulate (antagonize or agonize) the melatonin-signaling pathway are presented herein. It will be understood that the invention is not so limited. Indeed, often assays well known in the art can be used in order to identify such compounds.

It should be understood that candidate compounds to be tested according to the method of the present invention include non-peptides drug candidates (small molecules) as well as peptides targeting defective proteins involved in the melatonin-signaling pathway impairment, or oligonucleotides such as antisens molecules targeting a defective gene involved in the melatonin-signaling pathway impairment.

Other objects, advantages and features of the present invention will become more apparent upon reading of the following non-restrictive description of preferred embodiments thereof, given by way of example only with reference to the accompanying drawings.

DESCRIPTION OF SPECIFIC EMBODIMENTS

Figure 1:
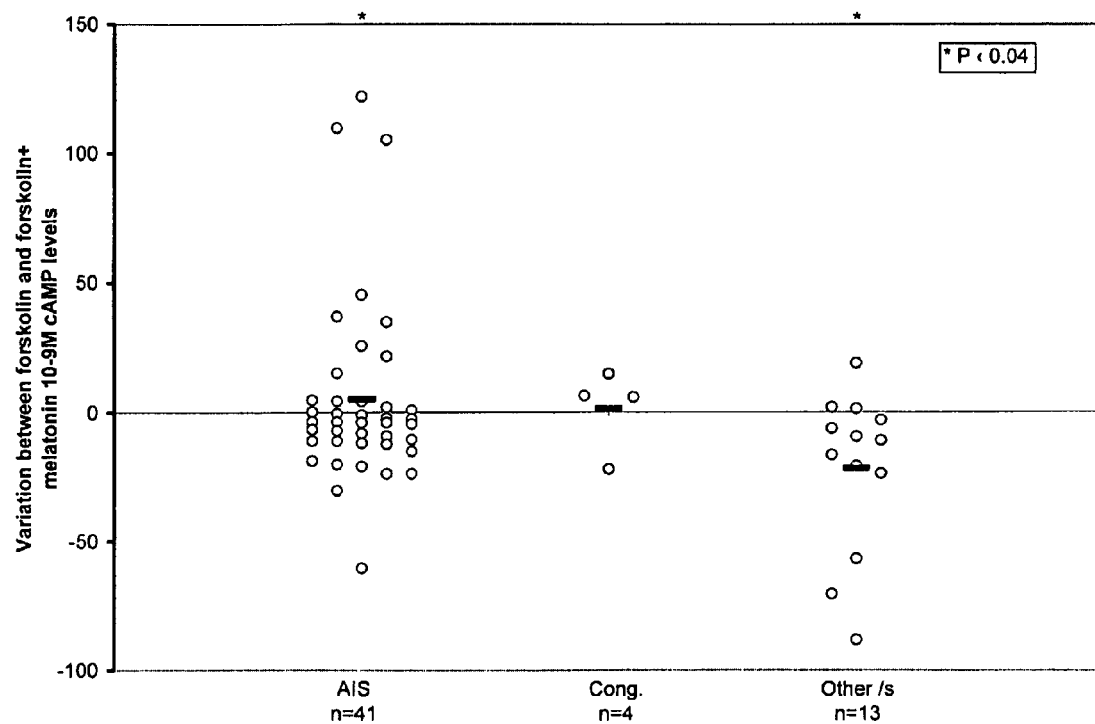
FIG. 1 graphically shows the inhibitory effect of melatonin on adenylyl cyclase activity in human normal osteoblasts and in AIS osteoblasts. Distribution of single data points obtained for each AIS patients and control subjects (congenital scoliosis, cong; and other scoliotic type, other/s) tested at physiological dose of melatonin ($10^{-9}$M) on forskolin-stimulated osteoblasts. The black bars represent the mean of each group.

In vitro assays were performed with bone-forming and muscle-forming cells isolated from 41 patients with adolescent idiopathic scoliosis (AIS) patients and 17 control subjects demonstrating that patients with this disease exhibit a dysfunction of the melatonin-signaling pathway in tissues targeted by this hormone.

Osteoblast and myoblast cultures prepared from specimens obtained intraoperatively during spine surgeries were used to test the ability of melatonin and Gpp(NH)p, a GTP analogue, to block cAMP accumulation induced by forskolin. In parallel, melatonin receptors and Gi proteins functions were evaluated by immunohistochemistry, binding assays with [$^{125}$I]-iodomelatonin and by co-immunoprecipitation experiments. The cAMP assays demonstrated that melatonin-signaling was severely impaired in osteoblasts and myoblasts isolated from AIS patients allowing their classification in 3 distinct groups based upon their responsiveness to melatonin or Gpp (NH)p. Melatonin-signaling is clearly impaired in osteoblasts and myoblasts of all AIS patients and DD patients tested. Classification of AIS patients in 3 groups suggests the presence of distinct mutations interfering with the melatonin signal transduction. Post-translational modifications affecting Gi protein function should be considered as one possible mechanism.

Experimental data showed a melatonin-signaling dysfunction in osteoblasts and myoblasts isolated from 100% AIS patients tested.

Although the present invention has been described hereinabove by way of preferred embodiments thereof, it can be modified, without departing from the spirit and nature of the subject invention as defined in the appended claims.

Example 1

Clinical Characteristics of AIS Patients and Control Subjects from which Osteoblasts were Isolated The clinical characteristics of the examined AIS and control subjects are shown in Table 1.

TABLE 1

Clinical data on patients with adolescent idiopathic scoliosis and control subjects

| Case | Diagnostic | Curve Pattern | Gender | Age at surgery | Cobb Angle | Heredity | Basal cAMP | Induced cAMP | Melatonin Group |
|---|---|---|---|---|---|---|---|---|---|
| 1 | AIS | L lumbar | M | 16.33 | 45 | Yes | 0.01 | 12.06 | 3 |
| 2 | AIS | L thoracolumbar | F | 16.17 | 37 | Yes | 2.01 | 21.77 | 2 |
| 3 | AIS | L thoracolumbar | F | 17.08 | 47 | No | 0.10 | 15.84 | 2 |
| 4 | AIS | L thoracolumbar | F | 17.92 | 50 | na | 0.16 | 3.81 | 1 |
| 5 | AIS | R thoracic | M | 16.00 | 49 | No | 0.10 | 24.52 | 1 |
| 6 | AIS | R thoracic | M | 15.42 | 48 | No | 0.01 | 3.50 | 2 |
| 7 | AIS | R thoracic | M | 13.25 | 75 | No | 0.01 | 11.90 | 2 |
| 8 | AIS | R thoracic | F | 14.92 | 54 | Yes | 0.10 | 16.36 | 1 |
| 9 | AIS | R thoracic | F | 14.92 | 30 | Yes | 0.10 | 19.85 | 1 |
| 10 | AIS | R thoracic | F | 16.67 | 57 | Yes | 0.40 | 12.20 | 2 |
| 11 | AIS | R thoracic | F | 12.67 | 67 | Yes | 0.88 | 48.95 | 3 |
| 12 | AIS | R thoracic | F | 17.25 | 53 | Yes | 0.26 | 31.71 | 3 |
| 11 | AIS | R thoracic | F | 15.25 | 53 | No | 0.70 | 20.37 | 2 |
| 14 | AIS | R thoracic | F | 18.42 | 34 | No | 0.46 | 61.08 | 2 |
| 15 | AIS | R thoracic | F | 13.75 | 61 | No | 0.01 | 14.70 | 2 |
| 16 | AIS | R thoracic | F | 13.00 | 48 | No | 0.10 | 15.84 | 2 |
| 17 | AIS | R thoracic | F | 16.25 | 60 | No | 0.01 | 13.35 | 2 |
| 18 | AIS | R thoracic | F | 14.75 | 67 | No | 0.03 | 3.41 | 2 |
| 19 | AIS | R thoracic | F | 15.08 | 30 | No | 0.40 | 16.78 | 3 |
| 20 | AIS | R thoracic | F | 14.67 | 32 | No | 0.10 | 21.20 | 3 |
| 21 | AIS | R thoracic | F | 15.83 | 43 | No | 0.10 | 20.81 | 3 |
| 22 | AIS | R thoracolumbar | M | 18.67 | 61 | Yes | 0.10 | 22.74 | 1 |
| 23 | AIS | R thoracolumbar | F | 14.08 | 50 | Yes | 0.90 | 18.70 | 3 |
| 24 | AIS | R/L double scoliosis | M | 17.25 | 46-30 | Yes | 0.10 | 4.45 | 1 |
| 25 | AIS | R/L double scoliosis | M | 17.17 | 70-50 | No | 1.90 | 67.78 | 3 |
| 26 | AIS | R/L double scoliosis | F | 14.17 | 70-48 | Yes | 0.03 | 51.64 | 2 |
| 27 | AIS | R/L double scoliosis | F | 12.75 | 53-55 | Yes | 0.19 | 7.25 | 2 |
| 28 | AIS | R/L double scoliosis | F | 14.75 | 41-50 | Yes | 0.10 | 9.18 | 3 |
| 29 | AIS | R/L double scoliosis | F | 16.25 | 51-30 | No | 0.10 | 69.91 | 1 |
| 30 | AIS | R/L double scoliosis | F | 18.92 | 29-35 | No | 0.28 | 5.39 | 2 |
| 31 | AIS | R/L double scoliosis | F | 14.33 | 57-65 | No | 1.20 | 63.40 | 2 |
| 32 | AIS | R/L double scoliosis | F | 19.17 | 45-60 | No | 0.10 | 11.49 | 2 |
| 33 | AIS | R/L double scoliosis | F | 11.75 | 74-56 | No | 0.10 | 11.47 | 2 |
| 34 | AIS | R/L double scoliosis | F | 11.42 | 57-38 | No | 0.10 | 14.64 | 2 |
| 35 | AIS | R/L double scoliosis | F | 18.33 | 23-35 | No | 0.41 | 2.30 | 2 |
| 36 | AIS | R/L double scoliosis | F | 14.33 | 90-66 | No | 0.36 | 4.84 | 2 |
| 37 | AIS | R/L double scoliosis | F | 12.58 | 61-46 | No | 0.23 | 27.28 | 3 |
| 38 | AIS | R/L double scoliosis | F | 15.08 | 90-90 | No | 0.20 | 26.53 | 3 |
| 39 | AIS | R/L double scoliosis | F | 14.33 | 56-53 | No | 0.01 | 17.04 | 3 |
| 40 | AIS | R/L double scoliosis | F | 13.50 | 48-42 | No | 0.48 | 4.94 | 3 |
| 41 | AIS | R/L double scoliosis | F | 12.83 | 59-57 | No | 0.10 | 24.99 | 3 |
| 42 | Congenital | L lumbar | F | 18.42 | 53 | No | 0.01 | 1.00 | 2* |
| 43 | Congenital | R thoracic | M | 14.17 | 45 | No | 0.08 | 12.26 | 2* |
| 44 | Congenital | R thoracic | M | 13.08 | 70 | No | 0.95 | 55.36 | 2* |
| 45 | Congenital | R thoracic | F | 7.42 | 75 | No | 0.10 | 6.74 | 2* |
| 46 | Cancer/spine | none | F | 10.00 | 0 | No | 0.10 | 45.34 | Control |
| 47 | Cancer/spine | L thoracic | F | 16.33 | 19 | No | 0.12 | 19.55 | Control |
| 48 | Chiari | L thoracic | M | 19.92 | 51 | Yes | 0.32 | 15.19 | Control |
| 49 | DMD | none | M | 14.00 | 0 | No | 0.16 | 8.80 | Control |
| 50 | encéphalopath | R/L double scoliosis | M | 17.67 | 60-30 | No | 0.10 | 18.24 | Control |
| 51 | Marfan | L thoracolumbar | F | 19.42 | 38 | No | 0.10 | 8.00 | Control |
| 52 | Marfan/spondylo | R/L double scoliosis | F | 12.92 | 0 | Yes | 0.09 | 15.51 | Control |
| 53 | NF/scoliosis | R thoracolumbar | F | 15.75 | 115 | No | 0.10 | 21.48 | Control |
| 54 | Noonan | R thoracic | F | 18.75 | 49 | No | 0.01 | 13.97 | Control |
| 55 | spondylo | L lumbar | F | 19.00 | 0 | No | 0.10 | 15.34 | Control |
| 56 | spondylo | R lumbar | F | 16.42 | 0 | No | 0.10 | 36.20 | Control |
| 57 | spondylo | R thoracolumbar | M | 14.50 | 0 | No | 0.10 | 5.95 | Control |
| 58 | Traumatic cyphosis | R thoracic | F | 17.75 | 40 | No | 0.01 | 9.29 | Control |

AIS: adolescent idiopathic scoliosis; R, right; L, left; na, not available; NF, neurofibromatosis
Basal and induced cAMP values are given as pmoles/$1 \times 10^5$ cells

TABLE 2

Clinical data associated with individual AIS groups

| Patients | Age | Cobb's angle | Heredity | Basal cAMP | Induced cAMP |
|---|---|---|---|---|---|
| Groupe 1 | | | | | |
| F 57% | 15.5 | 48°-30° | 4/7 (57%) | 0.11 | 23.09 |
| M 43% | 17 | | | | |
| Groupe 2 | | | | | |
| F 79% | 14.2 | 54°-47° | 1/14 (7%) | 0.20 | 15.15 |
| M 21% | 16 | | | | |

TABLE 2-continued

Clinical data associated with individual AIS groups

| Patients | Age | Cobb's angle | Heredity | Basal cAMP | Induced cAMP |
|---|---|---|---|---|---|
| Groupe 3 | | | | | |
| F 75% | 14.3 | 55°-52° | 3/8 (38%) | 0.42 | 28.51 |
| M 25% | 16.5 | | | | |

Controls mean values basal cAMP: 0.12; induced cAMP: 7.58

Example 2

Study Design for Assays Performed with Osteoblasts

The melatonin signal transduction pathway functionality was investigated in osteoblasts from patients with clinically well-defined AIS (n=41) and compared with age- and gender-matched subjects presenting or not a scoliosis (n=17) (Table 1).

Example 3

Isolation of Human Osteoblasts

Osteoblasts were obtained intraoperatively from bone fragments reduced in smaller pieces mechanically with a bone cutter in sterile conditions and incubated at 37° C. in 5% $CO_2$ in a 100 mm culture dish in presence of DMEM medium containing 10% FBS (certified FBS, Invitrogen, Burlington, ON, Canada) and 1% penicillin/streptomycin (Invitrogen). After a 30-day period, osteoblasts emerged from the bone pieces were separated at confluence from the remaining bone fragments by trypsinization.

Example 4

Assay for Detecting Melatonin-Signaling Pathway in AIS Osteoblasts-cAMP Accumulation Using Melatonin as Known Agonist of the Melatonin-Signaling Pathway Osteoblasts from patients with AIS and control subjects were seeded in quadruplet on 24-wells plate ($1 \times 10^5$ cells/well) and incubated either with the vehicle alone, dimethyl sulphoxide (DMSO, Sigma™, Oakville, ON, Canada) or the diterpene forskolin ($10^{-5}$M, Sigma) to stimulate the cAMP formation. Inhibition curves of cAMP production were generated by adding melatonin to the forskolin-containing samples in concentrations ranging from $10^{-11}$M to $10^{-5}$M in a final volume of 1 ml of DMEM media with 0.5% bovine serum albumin (BSA, Sigma™). After a 30-minute incubation at 37° C., the cells were lysed and the sample centrifuged at 4° C. The cAMP content was determined in 200 µl aliquot of the supernatant using an enzyme immunoassay kit (Amersham-Pharmacia Biosciences, Mississauga, ON, Canada). All assays were performed in duplicate.

Figure 2:
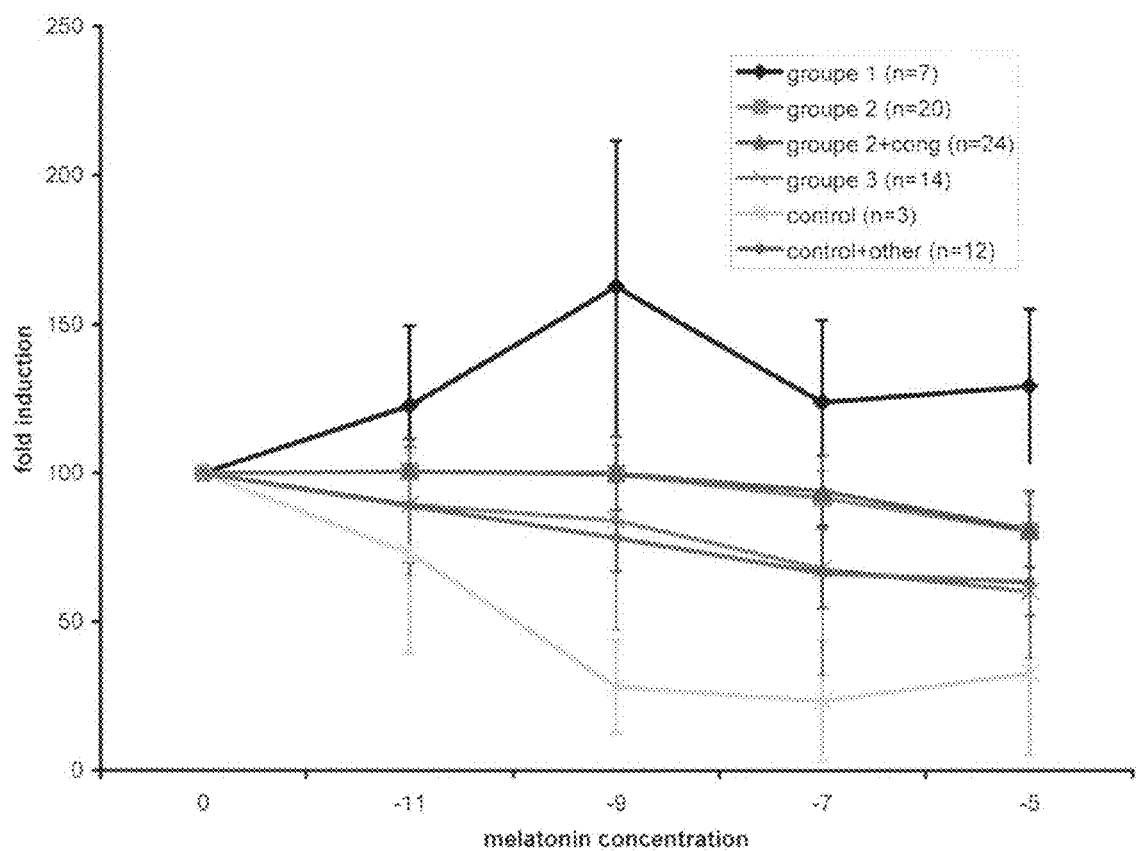
FIG. 2 graphically shows the inhibitory effect of melatonin on adenylyl cyclase activity in human normal osteoblasts and in AIS osteoblasts. Representative experiments showing the effect of increasing concentrations of melatonin ($10^{-11}$ to $10^{-5}$M) on forskolin-stimulated adenylyl cyclase activity in osteoblasts from control subject and patients with AIS (group 1, 2 and 3). Data are expressed as mean±SEM.

In osteoblasts from control subjects, melatonin produced a dose-dependent inhibition of forskolin-stimulated adenylyl cyclase activity detectable by a reduction of cAMP levels of about 60-70% (FIG. 1-2). In contrast, osteoblasts from patients with AIS showed a lack of inhibition of forskolin-stimulated adenylyl cyclase activity by melatonin (FIG. 1-2). The distributions of single data points obtained with patients with AIS, in comparison with control subjects are reported in FIG. 1. Further analysis allowed classifying patients with AIS into 3 distinct groups according to their osteoblast responsiveness to melatonin treatment (FIG. 2). In group 1, melatonin increased cAMP accumulation in treated osteoblasts, which contrasted with the normal inhibitory values obtained with control subjects (FIG. 2). In group 2, osteoblasts did not response to melatonin since no significant inhibition of cAMP accumulation was observed even at pharmacological dose ($10^{-7}$M) or higher ($10^{-5}$M) as illustrated by the cAMP curve inhibition (FIG. 2). Finally, the third group showed only a weak response toward melatonin treatment, although at physiological dose ($10^{-9}$M) no significant inhibition was measured (FIG. 2). Under standard assay conditions, basal and induced cAMP levels increased from group 1 to group 3 when compared to control subjects (data not shown).

In addition, 57% of the patients in the first group (1) showed the strongest heredity link when compared with the two other groups of patients. The second group of AIS patients did not respond to melatonin treatment even at pharmacological doses ($10^{-7}$M) and showed basal cAMP levels slightly elevated as compared with the first group and the control subjects. The third group remained resistant to melatonin, although at higher doses of melatonin, it was possible to measure some significant inhibitory effects on adenylyl cyclase activity. Both basal and forskolin-stimulated cAMP levels were increased in that particular group when compared with the other groups and the control subjects (Tables 1 and 2). Interestingly, the severity of the disease seems to be correlated by the augmentation of both basal and induced cAMP levels since the third AIS group is composed of the youngest mean age of female patients at the time of the surgery exhibiting also the highest Cobb's angle degrees pre-op in double scoliosis (Table 2). In spite of the heterogeneity of both groups, AIS patients displayed a more significant dysfunction of melatonin-signaling over the other types of scoliotic patients. Comparison with control subjects exhibiting also a scoliosis suggested that spinal deformities observed in distinct diseases and syndromes could share a common pathogenic mechanism interfering with the melatonin signal transduction.

Example 5

Assay for Detecting Melatonin-Signaling Pathway Impairment in AIS Osteoblasts—cAMP Accumulation Using GTP or Gpp(NH)p as Known Agonists of The Melatonin-Signaling Pathway The functionality of Gi proteins was assessed by investigating their ability to inhibit adenylyl cyclase activity in osteoblasts. To obtain inhibition curve of cAMP production the non-hydrolysable analogue of GTP, Gpp(NH)p (guanilyl 5'-imidophosphate, Sigma™) was added to the forskolin-containing samples in concentrations ranging from 10 nM to 100 µM. The cAMP content was determined as described above in similar assays with melatonin.

In vitro assays with Gpp(NH)p reduced cAMP levels in osteoblasts from control subjects in contrast to patients with AIS tested, which showed no inhibitory effect for a majority of AIS patients. The distribution of single data points obtained from each patient is reported in FIG. 8. The values reported in FIG. 8 were detected after the administration of $10^{-9}$M Gpp(NH)p, a GTP non-hydrolysable analogue.

Figure 8:
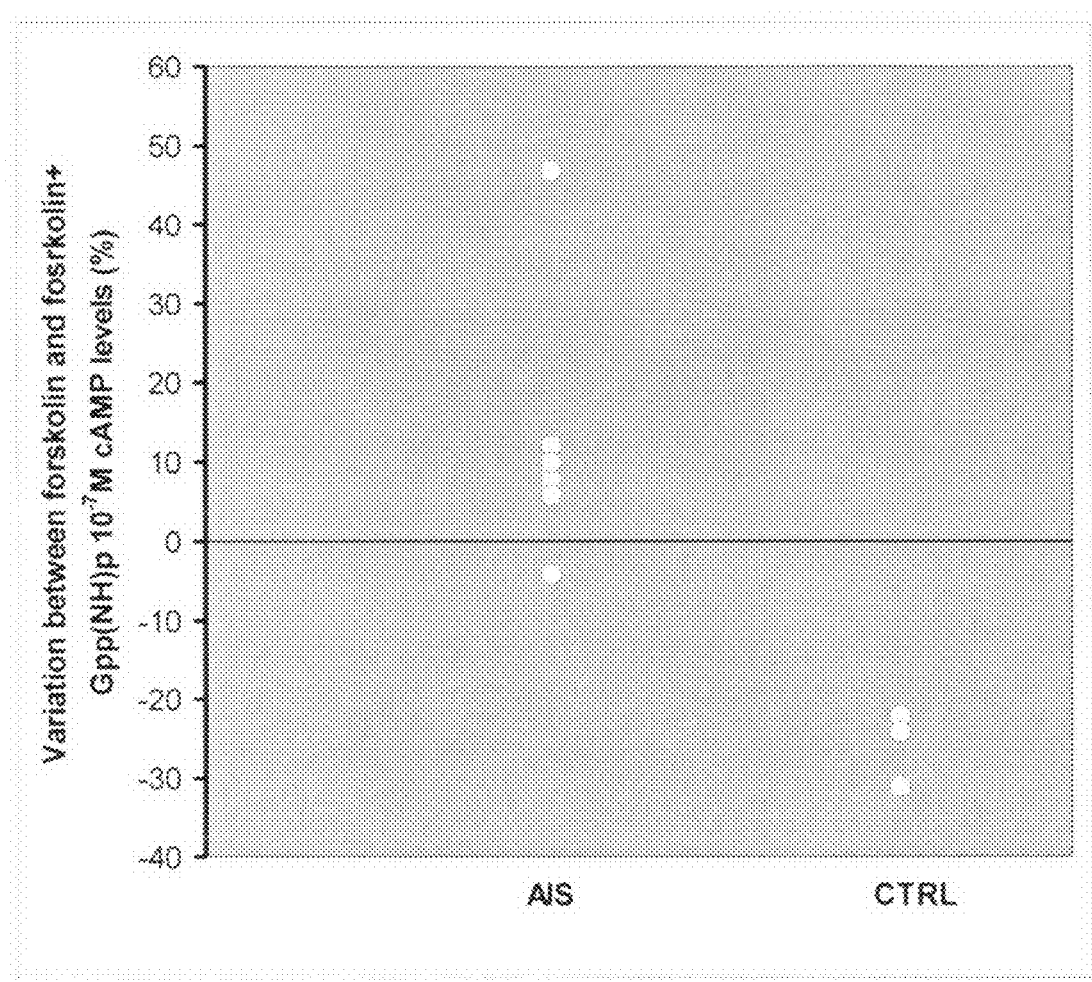
FIG. 8 shows the effect of Gpp(NH)p ($10^{-7}$M) on forskolin-stimulated adenylyl cyclase activity in osteoblasts from control subjects and in osteoblasts from patients with AIS. Distribution of single data points obtained from each patient with AIS and control subjects tested.

The ability of the non-hydrolysable GTP analogue to inhibit adenylyl cyclase activity was detected. This enzymatic activity was previously amplified by forskolin. The impaired capability to inhibit forskolin-stimulated adenylyl cyclase activity was also observed with the non-hydrolysable GTP analogue, Gpp(NH)p (FIG. 8). Considering the multiplicity of GTP-binding proteins present in osteoblasts (24), it may seem difficult to detect a defect in a particular G-protein subtype with the use of a GTP analogue. However, not only a preferential affinity of Gpp(NH)p towards Gi proteins in the range of concentrations used has been evidenced (25; 26), but also a widely different expression of each type of G protein is documented, indicating that Gi are commonly 10 times more abundant than Gs(24).

Analysis of the data obtained with the Gpp(NH)p assays revealed again the presence of three distinct groups although different groups of AIS patients (based upon the melatonin assays) are retrieved. This may suggest again that at least 3 distinct genes or type of mutations contribute to decrease or modify Gi proteins function in AIS, which matches well with the clinical variables associated with each AIS patients.

Example 6

Statistical Analysis

Results from the cAMP accumulation assays are given as the mean±SEM. Data were analyzed with StatView software.

Example 7

Level of Melatonin Receptors in Osteoblasts

Figure 7:
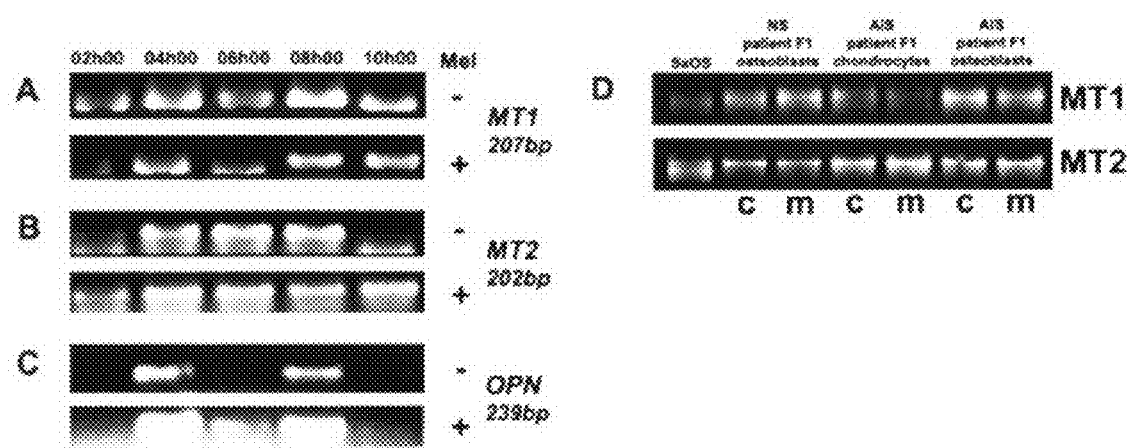
FIG. 7 shows the expression analysis of melatonin receptors in human osteoblasts.

Patients with AIS and control subjects were also investigated to exclude the possibility that melatonin signaling dysfunction observed in that assay could be secondary to a reduced level of melatonin receptors. RT-PCR were performed with specific primers corresponding to melatonin receptor subtypes, MT1 (panel A, FIG. 7), MT2 (panel B, FIG. 7) and OPN (panel C, FIG. 7) using 2 μg of RNA isolated every 2 h during a 24 h cycle from MC3T3-E1 cells treated (+) or not (−) with melatonin ($10^{-7}$M). Panel D, FIG. 7 represents a similar analysis with osteoblast cultures obtained from one scoliotic patient (AIS female, 15 year old) and a non-scoliotic subject (NS female, 15 year old) without (c) and with melatonin (m, 10-7M). PCR products were separated on a 1.5% agarose gel and visualized by ethidium bromide staining. Note that both melatonin receptor subtypes are expressed in MC3T3-E1 cells and in human osteoblasts but in MC3T3-E1 cells, only MT1 subtype is down regulated in presence of melatonin while MT2 subtype is the predominant form. No significant difference was observed between AIS and NS subjects. Expression analysis by RT-PCR and IHC experiments indicated no significant variation in melatonin receptor levels although it cannot be ruled-out that their function could be altered in AIS.

Example 8

Assay for Determining Mel Receptors Function and Distribution in Osteoblasts: Radioligand Binding and IHC Assays Radioligand-binding assays with 2-$^{125}$I-iodomelatonin and IHC assays with MT1 and MT2 specific antibodies were performed to assess whether the dysfunction of melatonin-signaling observed could be secondary to either a reduced level of melatonin receptors or to mutations affecting their function.

To determine whether or not melatonin receptor function is affected in osteoblasts from patients with AIS, total binding assays were conducted using the radioligand 2-[$^{125}$I] iodomelatonin (500 pM, Amersham-Pharmacia Biosciences) in the absence (total binding) or presence (non-specific binding) of melatonin (1 μM, Sigma™). All reactions were run in duplicate. The data were expressed as femtomoles of receptor per milligram of protein. Protein determination was made by the method of Bradford using BioRad™ protein assay reagents (BioRad, Mississauga, ON, Canada). Receptor subtype localization and distribution were determined in osteoblastic cells by immunohistochemistry (IHC) assays with anti-human MT1 and anti-human MT2 antibodies (kind gifts from Prof. F. Fraschini and Dr D. Angeloni, University of Milan, Italy).

Figure 3:
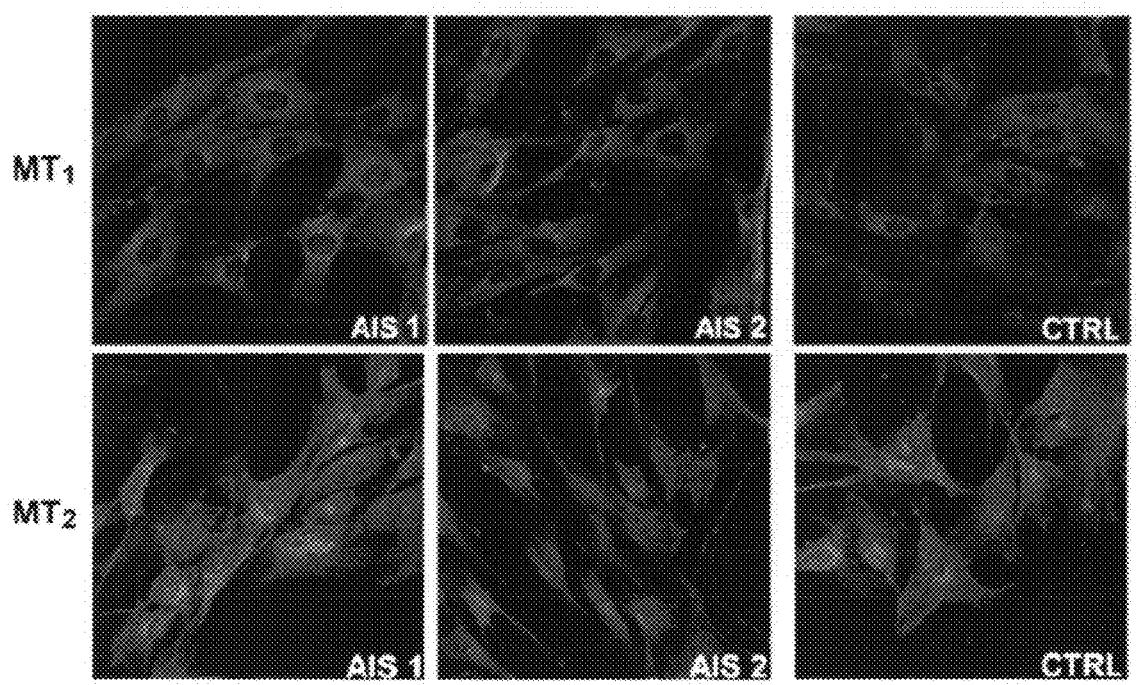
FIG. 3 illustrates through photographs the detection of MT1 and MT2 melatonin receptors in human osteoblasts from patients with AIS and from control subjects. Each panel illustrates representative IHC experiments performed with MT1 receptor antibodies (upper panels) and MT2 receptor antibodies (lower panels) on primary human osteoblast cultures prepared from patients with AIS (AIS1-2) and compared with a control subjects.
Figure 4:
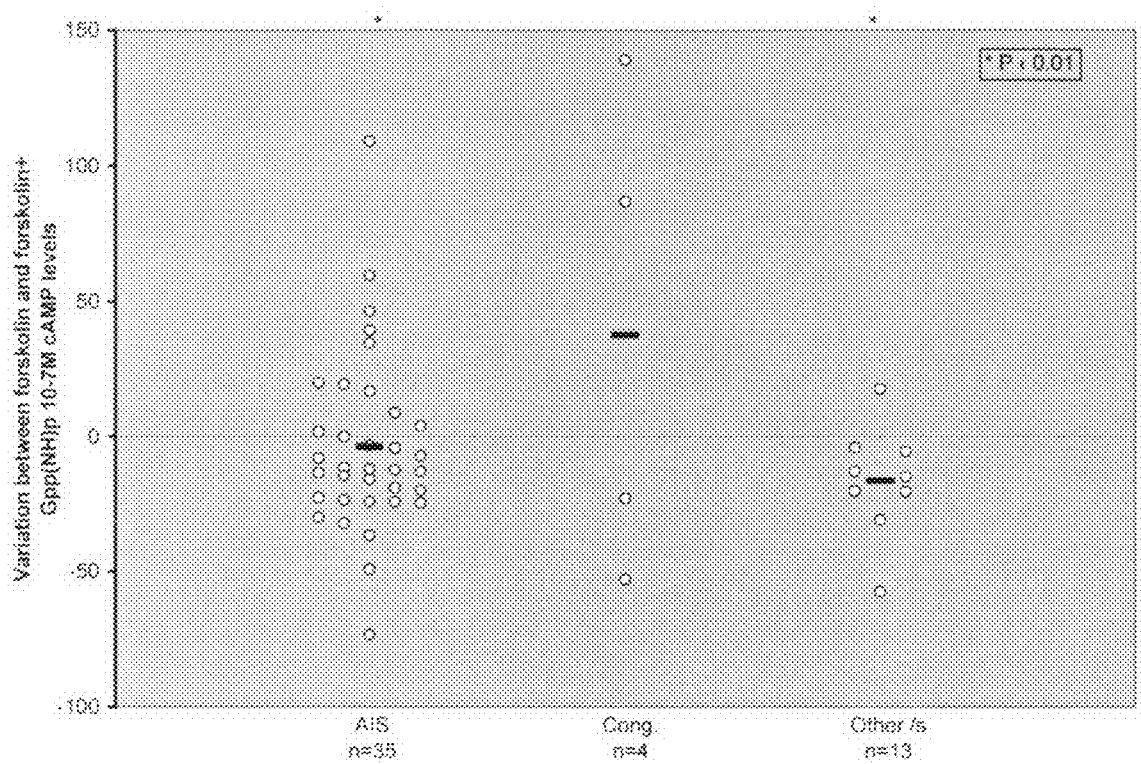
FIG. 4 graphically shows the Gpp(NH)p inhibitory effect on adenylyl cyclase activity on human osteoblasts from patients with AIS and on control subjects. Distribution of single data points obtained for each AIS patients and control subjects in presence of Gpp(NH)p ($10^{-7}$M) on forskolin-stimulated osteoblasts. The black bars represent the mean of each group.

Results obtained with the radioligand binding assays showed no significant variation in the function of melatonin receptors (data not shown). This correlated well with IHC analysis, which revealed no significant variation in the synthesis and distribution of both melatonin receptor subtypes in both patients with AIS and control subjects (FIG. 3).

Example 9

Figure 9:
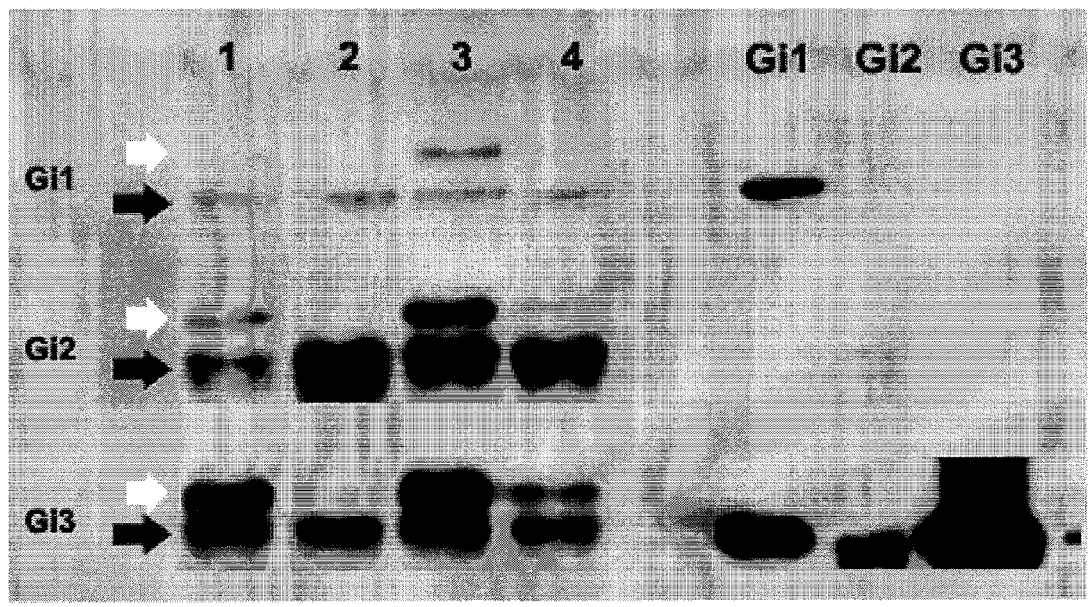
FIG. 9 shows Gi proteins coupled to MT2 melatonin receptor. Black and white arrows correspond to unphosphorylated and phosphorylated forms of Gi proteins respectively.

Assay for Determining Gi Protein Coupling to Individual Melatonin Receptors and Phosphorylation State in Osteoblasts Co-immunoprecipitation assays were performed with anti-MT1 and anti-MT2 specific antibodies (kind gifts of Dr Debora Angeloni and Prof Franco Fraschini, University of Milan, Italy) to identify Gi proteins coupled to individual melatonin receptor in human MG-63 osteoblasts (FIG. 9).

The specific antibodies were incubated with membrane fractions purified from osteoblasts untreated and treated with melatonin ($10^{-9}$M), genistein or herbimycin (1 μM, tyrosine kinase inhibitors, Sigma™) or sodium orthovanadate, $Na_3VO_4$, (1 mM, tyrosine phosphatase inhibitor, Sigma™) for at least 16 h. Presence of coupled Gi proteins in respective immune-complexes were determined by SDS-PAGE and Western blot with specific Gi antibodies (Santa Cruz Biotechnology Inc., Santa Cruz, Calif., USA) and phosphorylation status of these coupled Gi proteins were determined using anti-phosphoserine, phosphothreonine and phosphotyrosine antibodies (Sigma™) using the same membrane after stripping. Purified recombinant Gi proteins were used as control for antibody specificity.

Figure 5:
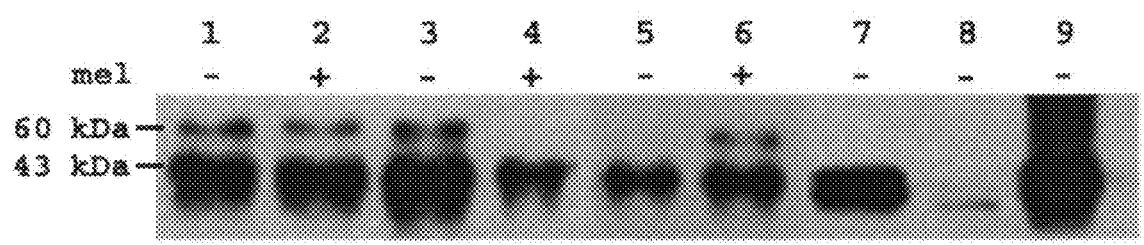
FIG. 5 illustrates through photographs the detection of Gi3 proteins coupled to MT2 receptors. Immunoblots were revealed with specific antibodies reacting with individual Gi with the exception of anti-Gi3 antibodies, which cross-react also with human Gi1 proteins. Note the presence of 60 kDa bands corresponding to phosphorylated Gi3 proteins. Lane 1 and 2 are from control subject (Marfan) not treated and treated with melatonin ($10^{-7}$ M) respectively. Lanes 3-4 and 5-6 come from two different AIS patients. Lanes 7-8-9 are positive control peptides for Gi1, Gi2 and Gi3 respectively.

These assays showed a predominant coupling of Gi3 proteins with MT2 receptor in purified osteoblast membrane fractions treated or not with melatonin (FIG. 9) Interestingly, Western blot analysis with Gi3 antibodies revealed the presence of an additional higher molecular weight band corresponding to a phosphorylated form of Gi3 proteins (the presence of 60 kDa bands corresponding to phosphorylated Gi3 proteins in FIG. 5).

Figure 10:
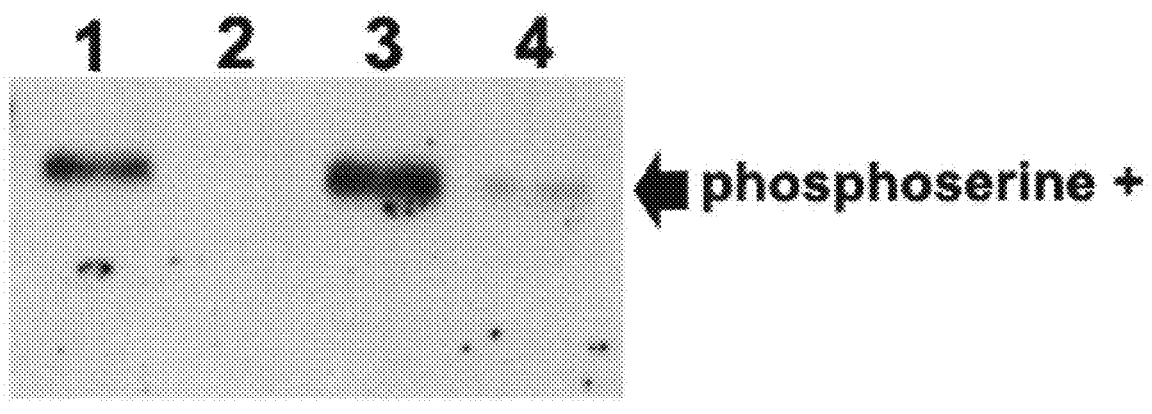
FIG. 10 shows the detection of phosphoserine residues in phosphorylated Gi proteins. The immunoblot in FIG. 9 was stripped and reprobed with antibodies recognizing antiphosphoserine residues. Numbering corresponds to cell cultures conditions: 1) untreated; 2) with melatonin; 3) with Na3VO4, a tyrosine phosphatase inhibitor; and 4) with genistein, a tyrosine kinase inhibitor.

Immunodetection assay with specific antibodies reacting with phosphoproteins confirmed the presence of at least one phosphoserine residue in those higher molecular weight Gi3 proteins (FIGS. 9, 10). Furthermore, similar assays with osteoblasts isolated from two AIS patients revealed a distinct phosphorylation pattern with and without melatonin addition. Western blot analysis performed with respective membrane fractions using antibodies reacting against individual Gi proteins did not reveal any significant variation in the level of the three Gi proteins present in human osteoblast (FIG. 5).

Figure 20:
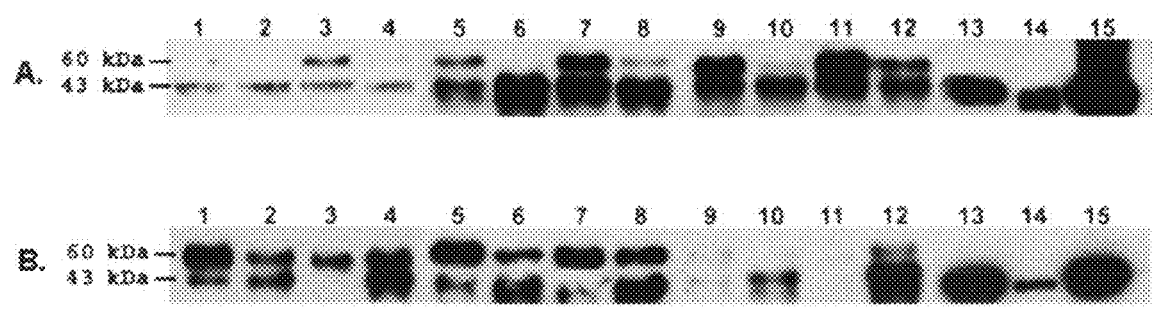
FIG. 20 shows Gi proteins coupled to MT2 melatonin receptor. The cells used were prepared from human MG-63 osteoblast culture (panel A) and osteoblast cultures from AIS patient (case 22 of Table 1, panel B)
Figure 21:
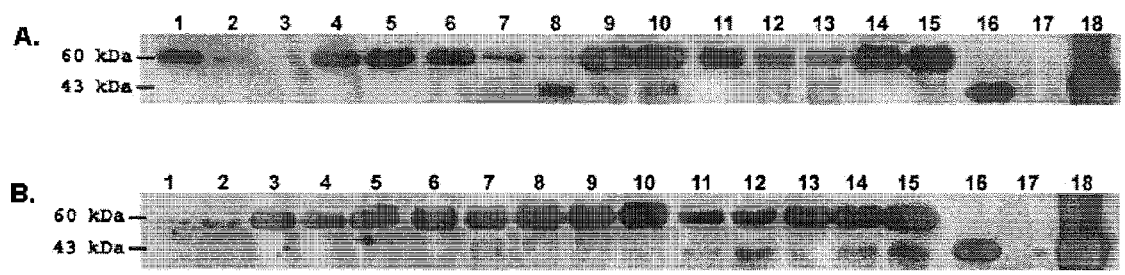
FIG. 21 shows Gi proteins coupled to MT2 melatonin receptor. The cells used were prepared from osteoblast cultures from AIS patient. Panel A, case 37 of Table 1; panel B, case 29 of Table 1.

FIG. 20 also illustrate how the phosphorylation pattern of cells isolated from patients with a melatonin-signaling impairment differs from those of control cells. Identification of Gi proteins coupled to MT2 melatonin receptor. Co-immunoprecipitation assays were performed with specific anti-MT2 antibodies using purified membrane fractions prepared from human MG-63 osteoblast culture (panel A) and osteoblast cultures from AIS patient (case 22, panel B) treated overnight in different conditions: 1-5-9) untreated; 2-6-10) with melatonin; 3-7-11) with $Na_3VO_4$, a tyrosine phosphatase inhibitor; and 4-8-12) with genistein, a tyrosine kinase inhibitor. Immunoblots were revealed with specific antibodies reacting with individual Gi with the exception of anti-Gi3 antibodies, which cross-react also with human Gi1 proteins. Lanes 1-4 with anti-Gi1; lanes 5-8 with anti-Gi2 and lanes 9-12 with anti-Gi3. Lanes 13-15 correspond to purified recombinant Gi1-3 proteins respectively and were used as control for antibody specificity. The 60 kDa and 43 kDa bands correspond to the phosphorylated (inactive) and unphosphorylated (active) forms of Gi protein, respectively. Note the changes in the phosphorylation patterns occurring in Gi proteins from AIS patient, showing increased phosphorylation and distinct regulation by kinase and phosphatase inhibitors tested. The results presented in FIG. 21 were obtained as described above and relate to cells isolated from other patients: human osteoblast cultures isolated from AIS patient (panel A, case 37 of Table 1; panel B, case 29 of Table 1) treated overnight in different conditions: 1-6-11) untreated; 2-7-12) with melatonin; 3-9-13) with $Na_3VO_4$, a tyrosine phosphatase inhibitor; 4-10-14) with genistein, a tyrosine kinase inhibitor; and 5-11-15) with herbimycine, another tyrosine kinase inhibitor. Lanes 1-5 with anti-Gi1; lanes 6-10 with anti-Gi2 and lanes 11-115 with anti-Gi3. Lanes 16-18 correspond to purified recombinant Gi1-3 proteins respectively and were used as control for antibody specificity. Note the changes in the phosphorylation patterns occurring in Gi proteins in both AIS patient, showing a predominant coupling with phosphorylated Gi proteins.

Expression analysis by RT-PCR did not show any significant variation in Gi mRNA levels encoding for the three Gi proteins present in human osteoblast (data not shown), although it cannot be excluded that such variation might occur at the protein level.

Figure 12:
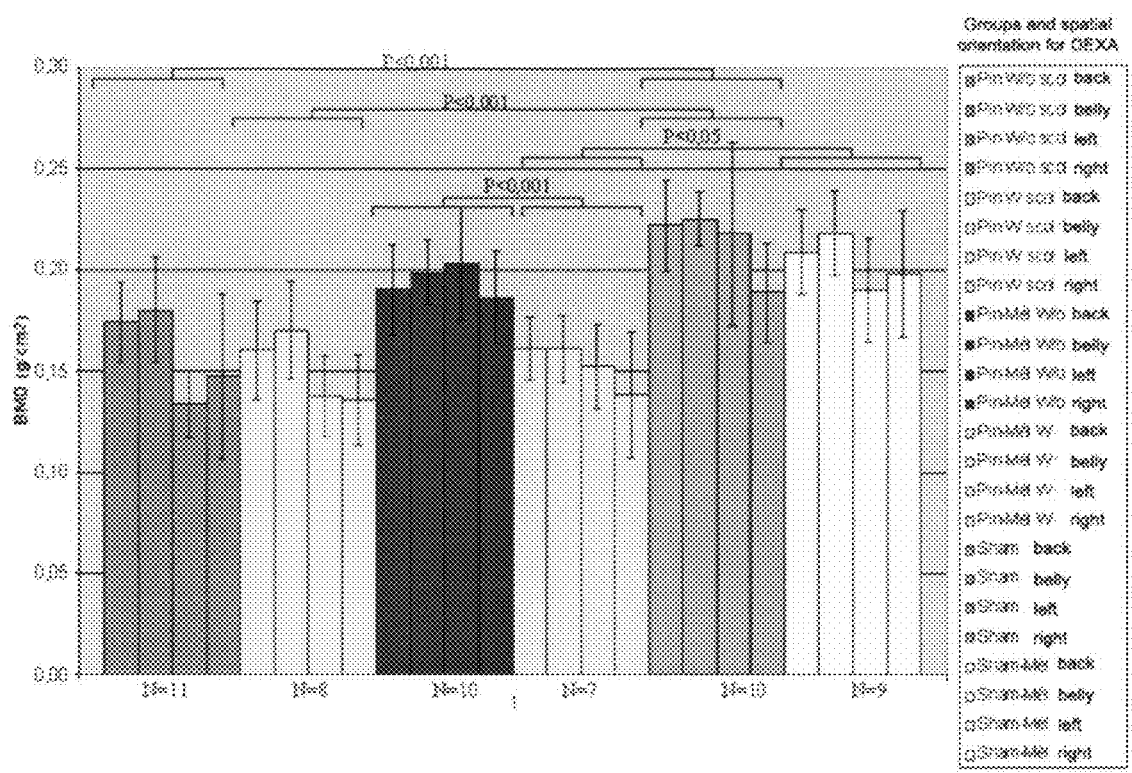
FIG. 12 graphically shows the bone mineral density in scoliotic and control chicken in four different plans.

The affinities of the three Gi proteins to the MT1 and MT2 receptors enabling them to be associated and pre-coupled to these receptors differ. The Gi3 has the strongest affinity to these receptors in absence or presence of melatonin, followed by Gi2 and then Gi1. In both conditions, only a weak interaction of Gi1 protein was detected with both receptor subtypes. Interestingly, in absence of melatonin, 2 forms of Gi3 and Gi2 proteins were detected suggesting that one of these forms could be phosphorylated (FIG. 12). Interestingly, overnight treatment of the cells with melatonin or genistein (a tyrosine kinase inhibitor) completely abolished the presence of both phosphorylated forms in MT1 or MT2 immune complexes. This suggests that a tyrosine phosphorylation regulates indirectly Gi proteins functions through the activation a downstream unknown serine kinase.

It cannot be ruled-out that changes in Gi proteins affinity for GTP and Gpp(NH)p could be triggered by post-translational modifications of Gi proteins involving serine residues phosphorylation. Phosphorylation of Gi proteins at their N-terminus is well known to block the formation of functional heterotrimers with Gβ and Gγ subunits preventing the inhibition of adenylyl cyclase activity either in presence of melatonin or Gpp(NH)p.

Example 10

Clinical Characteristics of AIS Patients and Control Subjects from which Myoblasts were Isolated The clinical characteristics of the examined AIS and control subjects are shown in Table 1 (cases 33, 22 and 8 in Table 1).

Example 11

Study Design for Myoblast Assays

The melatonin signal transduction pathway functionality was investigated in myoblasts from patients with clinically well-defined AIS (n=3, namely cases 33, 22 and 8 in Table 1) and compared with age- and gender-matched subjects presenting or not a scoliosis (Table 1).

Example 12

Isolation of Human Myoblasts

Myoblasts were obtained intraoperatively from normal and AIS patients and enzymatically dispersed, incubated, separated and put into cultures according to methods known in the art.

Example 13

Figure 15:
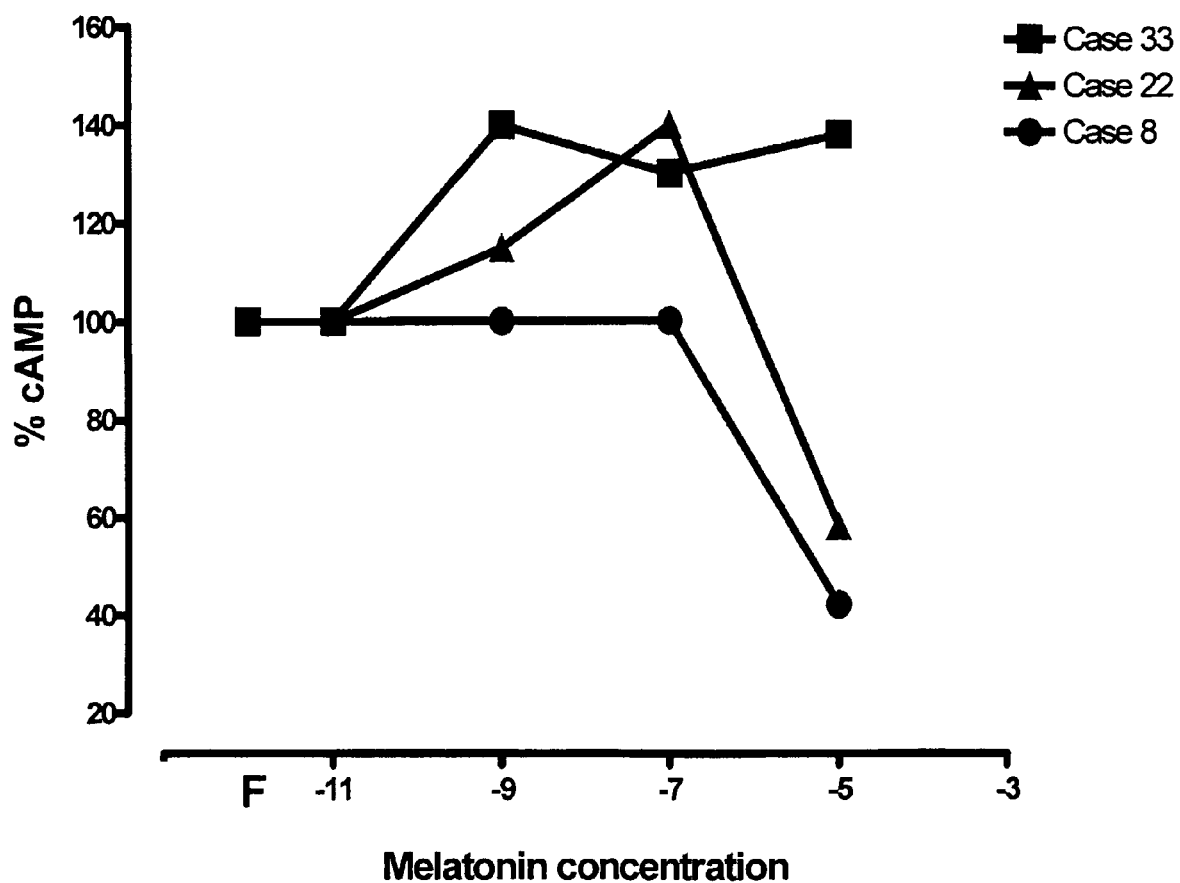
FIG. 15 graphically shows the inhibitory effect of melatonin on adenylyl cyclase activity in human normal myoblasts and in AIS myoblasts.

Assay for Detecting Melatonin-Signaling Pathway Impairment in AIS Myoblasts—Camp Accumulation Using Melatonin as Known Agonist of the Melatonin-Signaling Pathway Preliminary tests performed with skeletal myoblasts from showed the effect of increasing concentrations of melatonin ($10^{-11}$ to $10^{-5}$M) on forskolin-stimulated adenylyl cyclase activity in myoblasts isolated from AIS patients (cases 8, 22 and 23 in Table 1). These results (FIG. 15) show the incapacity of melatonin to inhibit cAMP accumulation induced by forskolin although only a treatment with a supra pharmacological dose of melatonin ($10^{-5}$M) is able in 2 cases to inhibit cAMP accumulation in myoblasts.

The functionality of melatonin signaling is assessed by investigating the ability of Gi proteins to inhibit stimulated adenylyl cyclase activity in intact skeletal myoblasts. Cells prepared from patients with AIS and control subjects are seeded in quadruplet on 24-wells plate ($1 \times 10^5$ cells/well), and incubated either with dimethyl sulphoxide (DMSO, Sigma™) or forskolin ($10^{-5}$M, Sigma™) to stimulate the cAMP formation. To obtain the inhibition curve of cAMP production, melatonin is added to the forskolin-containing samples in concentrations ranging from $10^{-11}$M to $10^{-5}$M in a final volume of 1 ml of DMEM media with 0.5% bovine serum albumin (BSA). After a 30-minute incubation at 37° C., the cells are lysed and the sample centrifuged at 4° C. The cAMP content is determined in 200 μl aliquot of the supernatant using an enzyme immunoassay kit (Amersham-Pharmacia Biosciences).

Example 14

Assay for Detecting Melatonin-Signaling Pathway Impairment in AIS Osteoblasts—cAMP Accumulation Using GTP or Gpp(NH)p as Known Agonists of the Melatonin-Signaling Pathway The functionality of Gi proteins is assessed by investigating their ability to inhibit adenylyl cyclase activity in myoblasts isolated from patients with AIS and control subjects. To obtain inhibition curve of cAMP production, the non-hydrolysable analogue of GTP, Gpp(NH)p (guanilyl 5'-imidophosphate, Sigma™) is added to the forskolin-containing samples in concentrations ranging from 10 nM to 100 µM. Protein determination is made by the method of Bradford using BioRad™ protein assay reagents (BioRad™) with BSA as standard. All assays are performed in duplicate.

Basal cAMP levels is obtained from untreated cells, while cells tested with forskolin alone corresponds to the induced levels. Standard curve for sensitivity and quantification is performed with standards provided by the manufacturer of respective assays. (23)

Example 15

Statistical Analysis for Assays with Myoblasts

Results from the cAMP accumulation assays are given as the mean±SEM. An analysis of variance (ANOVA), followed by Fisher's protected least significant difference (PLSD) procedure for post-hoc comparison is used to verify the significance between 2 means.

Example 16

Assay for Determining Mel Receptors Function and Distribution in Myoblasts: Radioligand Binding and IHC Assays Cellular localization and distribution of MT1 and MT2 melatonin receptors are determined on histological sections of human skeletal muscles obtained intraoperatively during spine surgeries and on skeletal myoblast cultures generated in parallel from patients with AIS and control subjects.

In order to determine whether or not melatonin receptors density or function could be affected in skeletal myoblasts from patients with AIS, total binding assays are conducted using the radioligand 2-[$^{125}$I] iodomelatonin (Amersham-Pharmacia Biosciences). This approach is also useful with the primary cell cultures to determine the effects of melatonin pre-treatment on receptor density and function ((47; 48)). Briefly, cells are washed with phosphate buffered saline (PBS), lifted in buffer, and pelleted by centrifugation. The cells are resuspended in Tris (50 mM, pH 7.4) buffer and then added to tubes containing 500 pM of 2-[125I] iodomelatonin in the absence (total) or presence (non-specific) of melatonin (1 µM) in a final reaction volume of 0.26 ml. Cells are then incubated for 1 h at room temperature and harvested by filtration over glass filters (Millipore™) pre-soaked in 10% polyethylenimine (Sigma™) and counted in a gamma counter. All reactions are run in duplicate. The data is expressed as femtomoles of receptor per milligram of protein. Protein determination is made by the method of Bradford using the BioRad™ protein assay reagents (BioRad™).

IHC experiments are performed with polyclonal antibodies reacting specifically with either the MT1 or MT2 receptor subtypes (kind gift from Dr Debora Angeloni and Prof Franco Fraschini, University of Milan, Italy) using a confocal microscope. In order to assess whether melatonin or estrogens could modify the cellular localization and/or distribution of MT1 or MT2 subtype, IHC experiments are performed with primary cell cultures treated with a physiological dose of melatonin ($10^{-9}$M) or estradiol ($10^{-10}$M).

Negative control for IHC is generated by omitting the primary antibody and by competition with specific blocking peptide. Positive controls are provided for IHC experiments and binding assays using stably transfected C2C12 myoblastic cells expressing constitutively MT1 or MT2 receptor. Specificity of each antibody has been already tested with human osteoblasts. In binding assays with [$^{125}$I] iodomelatonin, subtraction of non-specific binding obtained in presence of melatonin from the total binding generated with the radioligand alone determines the specific binding. However, MT1 and MT2 can bind this radioligand with almost the same affinity. Alternatively, the addition of luzindole (10 µM), a MT2 antagonist, could reveal indirectly the contribution of individual receptors in the total binding of 2-[$^{125}$I] iodomelatonin. All assays are performed in duplicate. Data obtained in total binding assays with the radioligand is analysed by Student's unpaired t-test. Significance is defined as $P<0.05$, and data will be analysed with StatView™ and Statistica™ softwares.

It cannot be ruled-out at this stage that scoliotic patients could display a distinct distribution of melatonin receptors. However, reduced receptor binding in situ could indicate potential interference by an unknown factor (calmodulin, estrogens etc.), that could be easily correlated at least for the estrogens by similar assay in vitro. A marked reduction of 2-[$^{125}$I] iodomelatonin binding in scoliotic sections could be caused by either a reduction in the number of a specific receptor subtype or a by a mutation reducing the affinity of this receptor. It is unlikely that the presence of serum in the in vitro binding assay may interfere with this assay since 10% FBS should contain less than $10^{-11}$M of melatonin.

Example 17

Assay for Determining Gi Protein Coupling to Individual Melatonin Receptors and Phosphorylation State in Myoblasts Muscle cells are grown to confluence in 10 cm tissue culture dishes, rinsed once with ice-cold PBS, and scraped off their plastic support. After sedimentation, the cell pellet are resuspended in 2 ml of buffer A (5 mM Tris-HCl pH 7.4/2 mM EDTA/protease inhibitors cocktail) and subsequently disrupted by sonication. Then, membranes are sedimented by centrifugation 450×g/5 min at 4° C. and the supernatant added on the top of 9 ml 35% sucrose cushion. Membranes will be sedimented by ultracentrifugation at 150,000×g/90 min. Purified membrane fraction sediment at the bottom of the sucrose cushion. Membrane fractions are resuspended in 1 ml of buffer B (50 mM Tris-HCl pH 7.4/5 mM MgCl$_2$) and incubated with or without ligand (melatonin) for 1 h at 25° C. For ligand-stimulated samples, all subsequent steps are performed in the continued presence of ligand. Thereafter, membranes are centrifuged at 18,000×g/30 min at 4° C. and washed once in 1 ml buffer C (75 mM Tris-HCl pH 7.4/12 mM MgCl$_2$/2 mM EDTA/protease inhibitors cocktail) and then resuspended in the same buffer containing 1% Triton X-100 (V/V), and agitated for 3 h at 4° C. Non-solubilized membrane proteins are removed by centrifugation at 18,000×g/30 min at 4° C. Immunoprecipitation of solubilized melatonin receptors are performed with gentle agitation overnight at 4° C. with antibodies (1:40) reacting specifically with either human MT1 or MT2 subtypes (kind gifts of Dr Debora Angeloni and Pr Franco Fraschini, Milan University, Italy), followed by a 6 h incubation at 4° C. with 50 µl of Protein-A agarose suspension (Sigma™) to immunoprecipitate by centrifugation the individual melatonin receptor. G proteins are dissociated from immune complexes by treatments with Gpp (NH)p (0.1 mM) for 1 h at 37° C. and are separated by 12% SDS-PAGE and transferred to nitrocellulose membranes.

Immunoblot are carried-out in TBST buffer containing 5% skim milk with commercially available antibodies recognizing individual Gi proteins (Gi1-3, Santa Cruz) and reactive bands are visualized using enhanced chemiluminescence. In parallel, similar assays are performed with purified membranes from cells treated overnight or less with physiological doses of melatonin, estradiol or with different kinase and phosphatase inhibitors such as tyrosine kinase inhibitors, tyrosine phosphatase inhibitors and PKC specific inhibitors. Additional immunodetection is performed with antibodies reacting against Gz proteins, a related Gi family member.

Example 18

Figure 6:
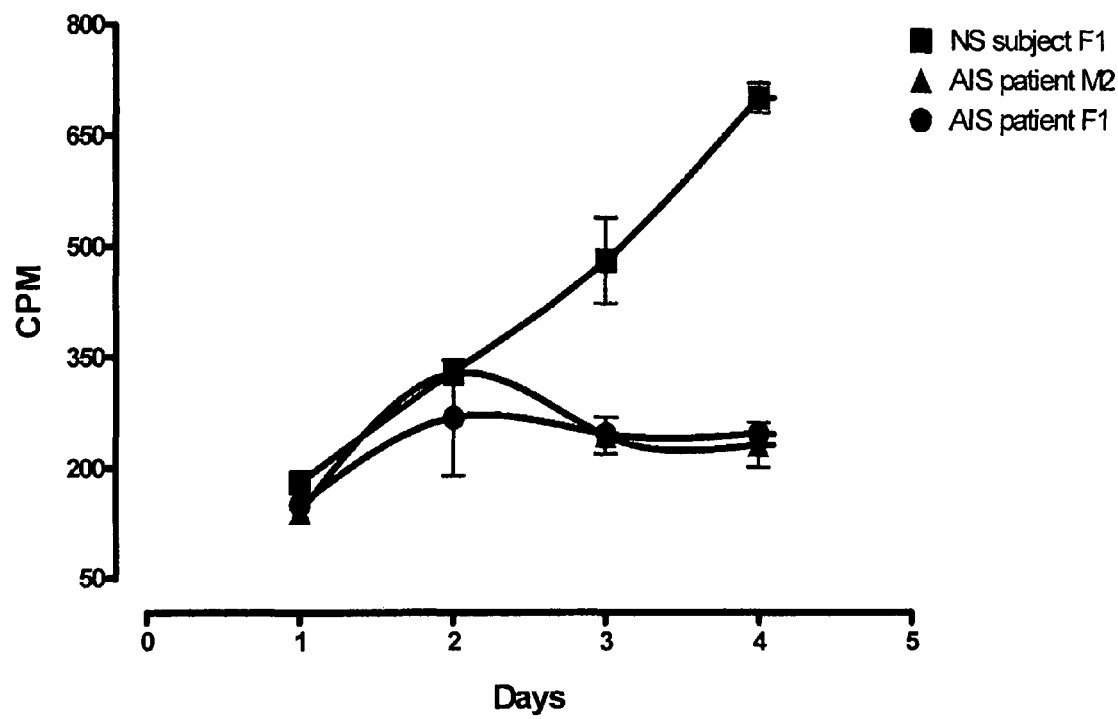
FIG. 6 graphically shows the proliferation of human normal osteoblasts and that of AIS osteoblasts through time-courses of [3H]thymidine uptake.

Assay for Detecting Melatonin-Signaling Impairment in Osteoblasts—Proliferation Assay An assay was performed to compare the proliferation of osteoblasts of normal subjects with that of scoliotic patients. In FIG. 6, Panel A represents time-courses experiments (triplicates) of [3H]-thymidine incorporation (cpm values in abscise axis) in human osteoblasts generated from bone specimens isolated from normal (NS) subject (F1/female 17 years old) and scoliotic patients (AIS M2/male 18 years old and F1/female, 17 years old) stimulated by a physiological dose of melatonin ($10^{-9}$M) used as known agonist of the melatonin-signaling pathway. This assay showed that normal osteoblasts growth rate increases linearly in response to a physiological dose of melatonin ($10^{-9}$M) while those from scoliotic patients did not respond to melatonin.

Example 19

Assay for Detecting Melatonin-Signaling Impairment in Lymphocytes—cAMP Accumulation Using Melatonin as Known Agonist of the Melatonin-Signaling Pathway Melatonin inhibition assays of cAMP accumulation assays induced by forskolin have been performed in vitro on human lymphocytes isolated from control subjects using 10 ml of blood or less. Anticoagulant-treated blood was layered on the FICOLL-PAQUE™ solution and centrifuged for a short period of time. Differential migration during centrifugation resulted in the formation of layers containing different blood cells. Because of their lower density, the lymphocytes were found at the interface between the plasma and the FICOLL-PAQUE™ with other slowly sedimenting particles (platelet and monocytes). The lymphocytes were then recovered from the interface and subjected to a short washing step with a balanced salt solution to remove any platelets, FICOLL-PAQUE™ and plasma. Then, the cells were counted and used to perform the cAMP assays described in Examples above. As is known from the literature, the lymphocytes have melatonin receptors at their surface. Results could be obtained in 3 h or less with this particular assay. This assay is advantageously rapid as compared to assays using osteoblasts (at least a month) because they do not require culture time.

Example 20

Assay for Detecting Melatonin-Signaling Impairment in Osteoclasts Derived from Monocytes/Lymphocytes Other functional assays with melatonin using osteoclasts derived from monocytes/lymphocytes fraction isolated from peripheral blood of AIS patients and control subjects are performed. Primary osteoclasts are derived from the peripheral blood of patients and non-scoliotic subjects using 10 ml of blood or less. Anticoagulant-treated blood is layered on the FICOLL-PAQUE™ solution and centrifuged for a short period of time. Differential migration during centrifugation results in the formation of layers containing different blood cells. Because of their lower density, the lymphocytes are found at the interface between the plasma and the FICOLL-PAQUE™ with other slowly sedimenting particles (platelet and monocytes). The lymphocytes are then recovered from the interface and subjected to a short washing step with a balanced salt solution to remove any platelets, FICOLL-PAQUE™ and plasma. The cells are then counted and seeded at high density ($1 \times 10^6$ cells per cm$^2$) onto artificial bone or dentin matrix in α-MEM with 10% FBS and antibiotics. After a few days, cells that remain adherent will start to differentiate into osteoclasts, forming large multinucleate cells after 15-20 days. Addition of melatonin ($10^{-9}$M to $10^{-7}$M) inhibits osteoclasts resorption activity, which is visualized by the absence of resorption pit in the bone matrix (i.e. absence of holes or fewer holes on the surface).

Figure 16:
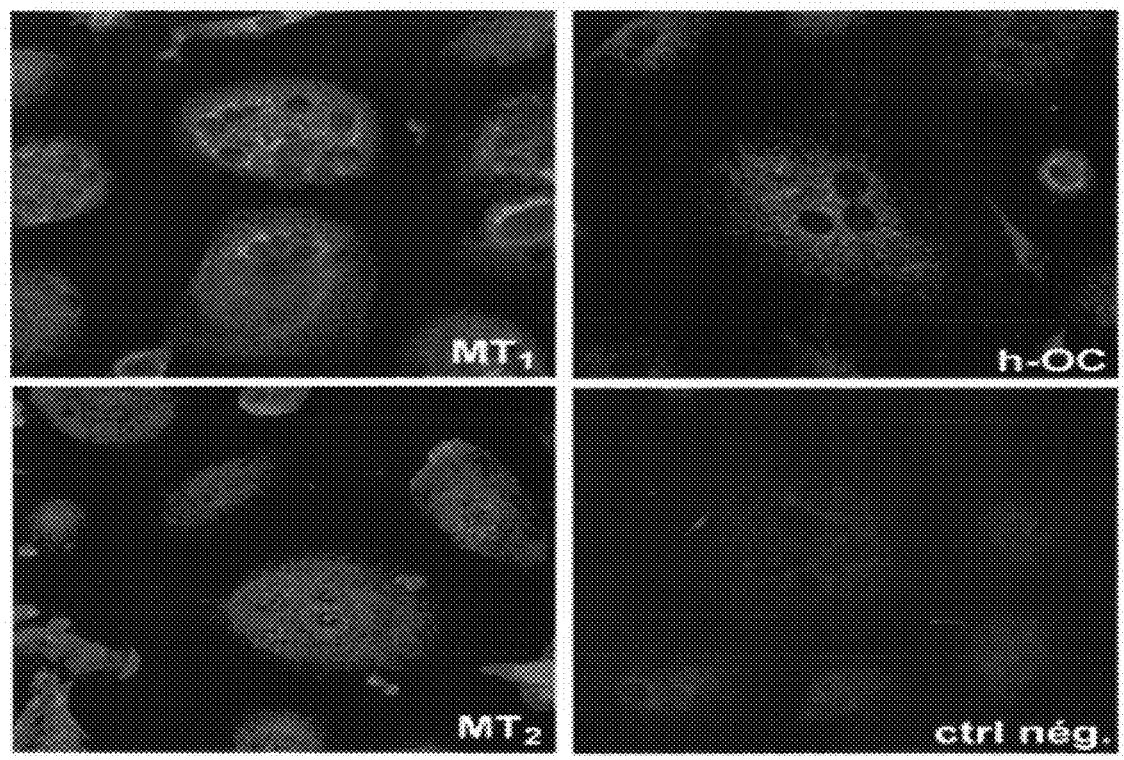
FIG. 16 illustrates through photographs the detection of MT1 and MT2 melatonin receptors in human osteoclasts from normal human subjects. Panels labeled MT1 and MT2 represent corresponding receptor subtype detected by IHC with specific primary antibodies and distinct secondary antibodies conjugated to different fluorochromes (red, phycoerythrin; green, FITC). The panel labeled h-OC corresponds to a human surface antigen specific for mature osteoclasts. Negative control has been generated by omission of the primary antibodies.
Figure 17:
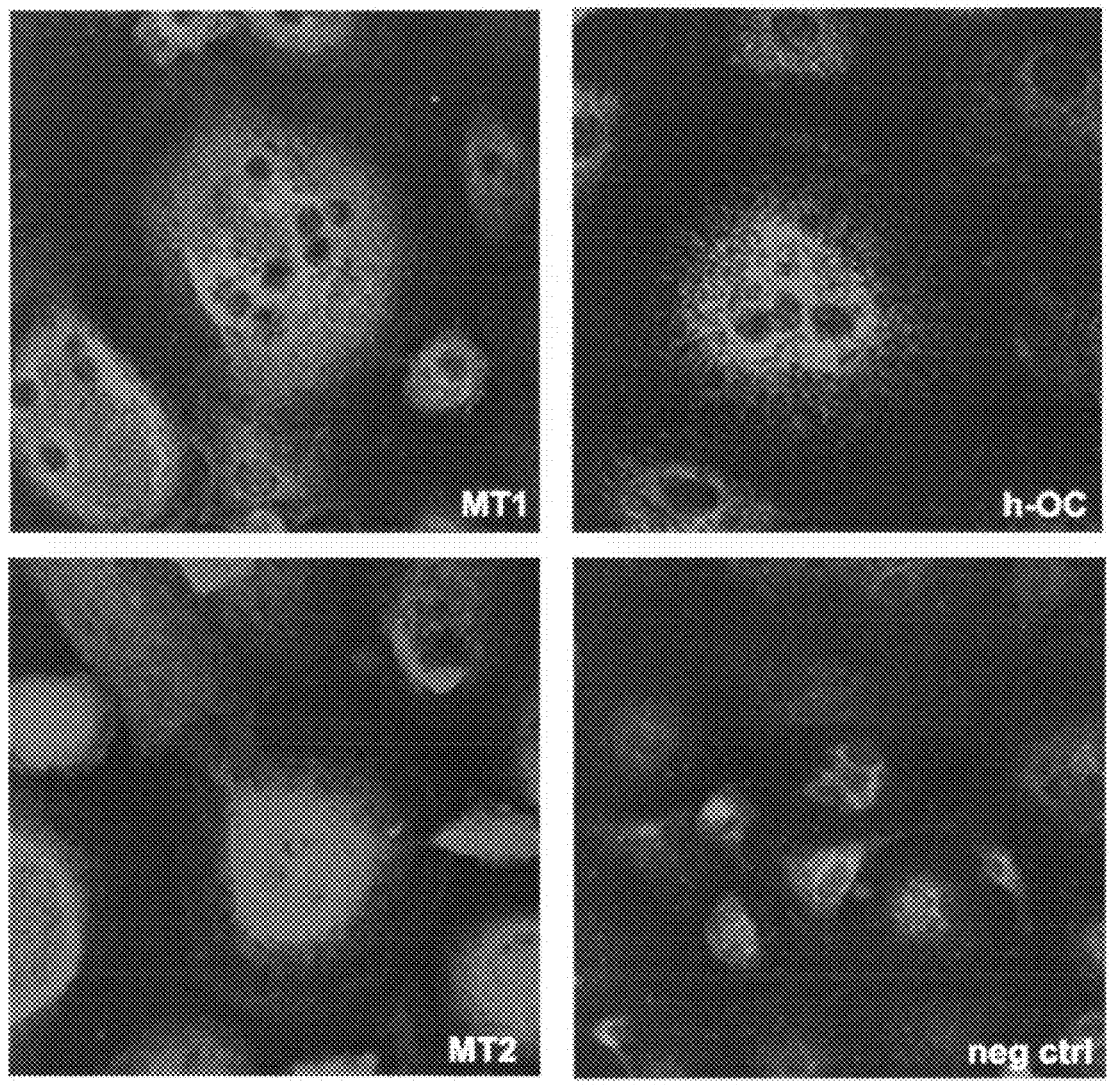
FIG. 17 illustrates through photographs the detection of MT1 and MT2 melatonin receptors in human osteoclasts from AIS human patients. Panels labeled MT1 and MT2 represent corresponding receptor subtype detected by IHC with specific primary antibodies and distinct secondary antibodies conjugated to different fluorochromes (red, phycoerythrin; green, FITC). The panel labeled h-OC corresponds to a human surface antigen specific for mature osteoclasts. Negative control has been generated by omission of the primary antibodies.

Different approaches (RT-PCR, immunohistochemistry) have demonstrated the presence of both melatonin receptor subtypes (MT1 and MT2) at the surface of human osteoclasts from normal subjects and from AIS patient (see FIGS. 16 and 17).

Figure 18:
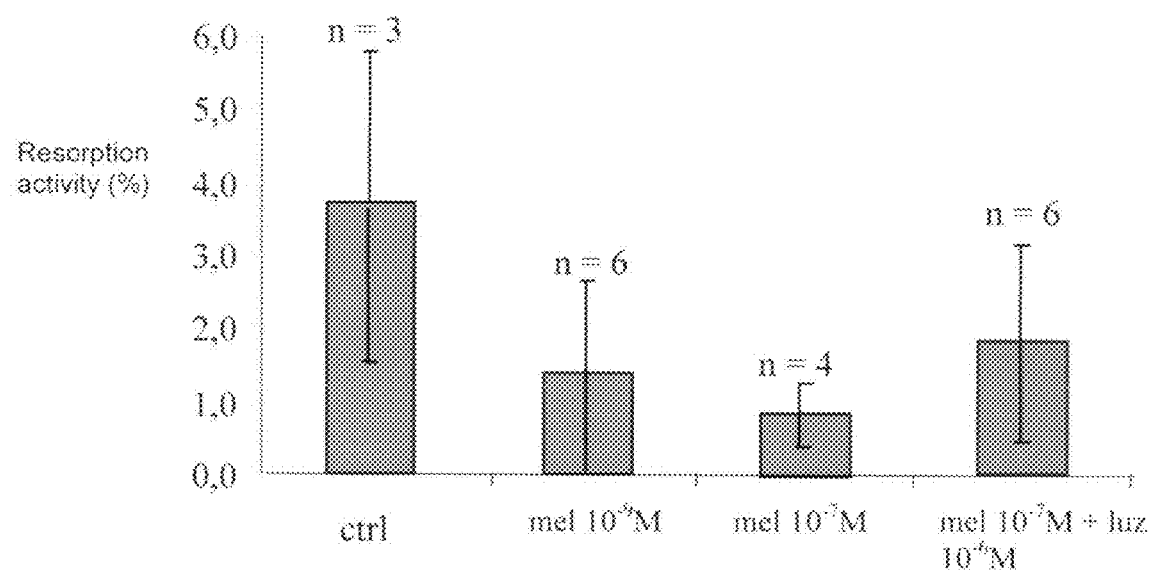
FIG. 18 graphically shows the measurement of osteoclasts activity (pit resorption assay) on bone matrix. The inhibitory effect of melatonin on osteoclasts activity was performed using normal human osteoclasts derived from peripheral blood. Mel, melatonin; luz, luzindole, a specific MT2 antagonist.

It was also evidenced that inhibitory activity of melatonin is mediated in osteoclasts through the MT2 receptor since the addition of luzindole, a MT2 specific antagonist prevents or reduces the inhibitory effect of melatonin on osteoclasts resorption activity (See FIG. 18). It is reasonably predicted that melatonin does not affect resorbing activity of osteoclasts isolated from animals with AIS or any related syndrome causing spinal deformities contrasting with the results observed in normal human osteoclasts.

Example 21

Melatonin-Signaling Pathway Modulated by Estradiol

Figure 19:
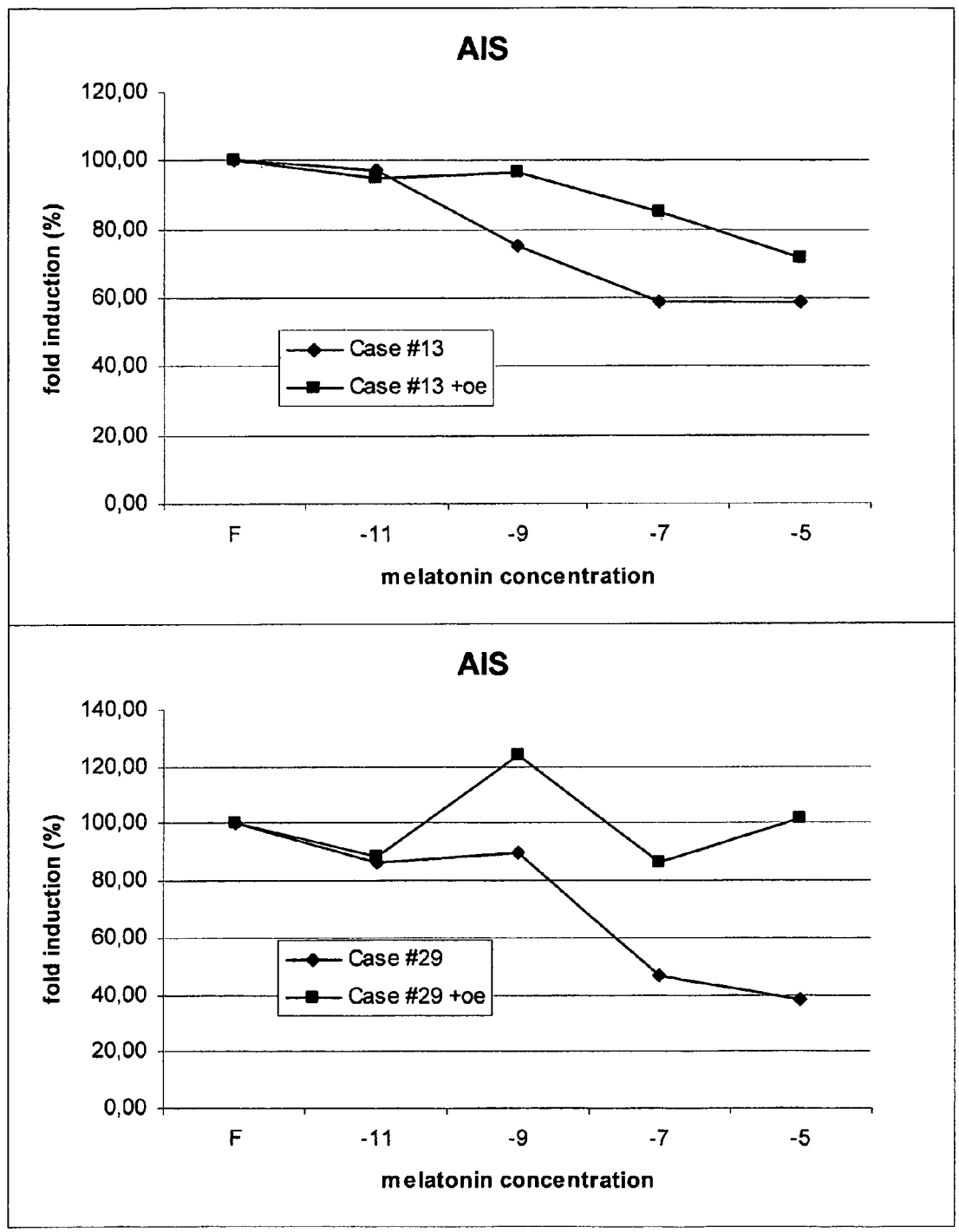
FIG. 19 graphically shows the effect of estrogen on the melatonin-signaling pathway impairment of patients with AIS.

A method of screening of the present invention was performed and identified estrogen as one compound able to modulate the melatonin-signaling pathway impairment in AIS patients. Experiments were performed showing the effect of increasing concentrations of melatonin ($10^{-11}$ to $10^{-5}$M) used as known agonist of melatonin-signaling pathway on forskolin-stimulated adenylyl cyclase activity in osteoblasts from two patients with AIS (group 3 see Table 2) treated or not with a physiological dose of estradiol ($10^{-10}$M). Results illustrated in panels A and B of FIG. 19 correspond to AIS patient numbered 13 and 29 in Table 1, respectively. It is apparent from this figure that the treatment with a physiological dose of estrogen (oe) is sufficient to further block the inhibitory effect of melatonin in scoliotic patients belonging to the AIS group 3 (see table 2).

Example 22

Evaluation of Bone Mineral Density in Scoliotic and Control Chicken

Figure 11:
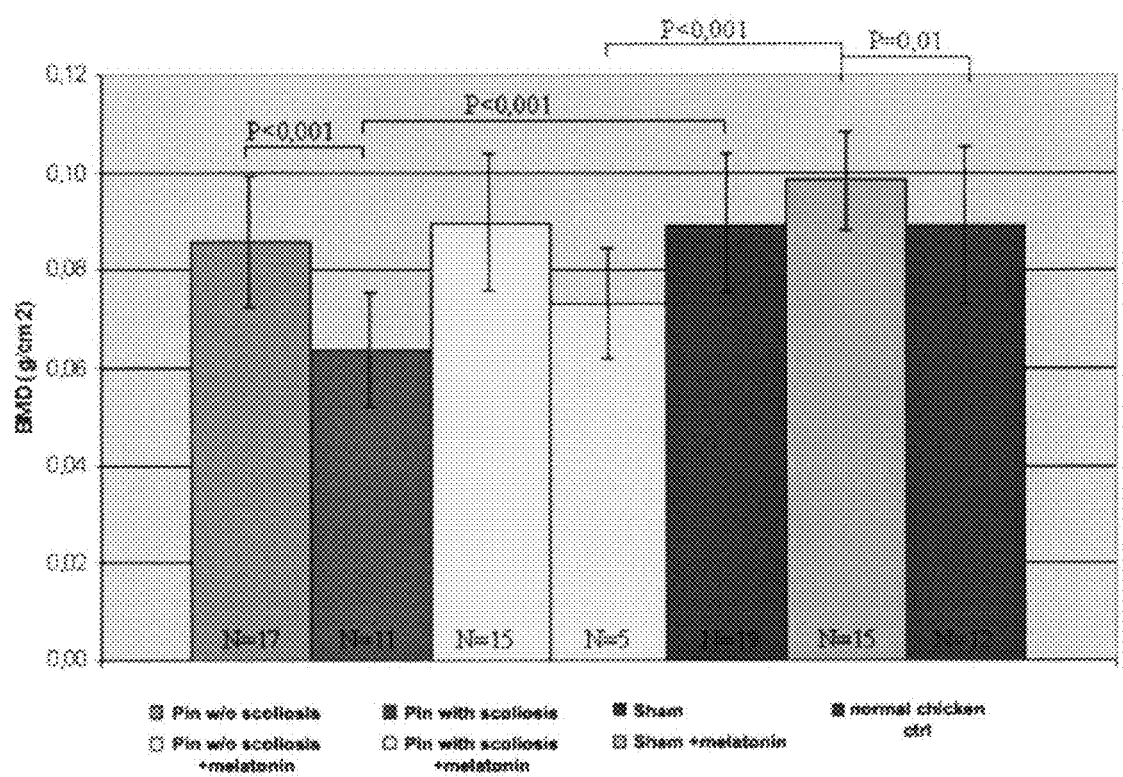
FIG. 11 graphically shows the bone mineral density in scoliotic and control chicken.

Non-invasive analyses were performed with a DEXA bone densitometer (PixiMUS™ II GE Lunar) and showed a significant decrease in bone mineral density (BMD) in both vertebrae and femur of all chicken although no difference was observed between those exhibiting a scoliosis and those without scoliosis (FIG. 11-12). Note that in our surgical conditions the rate of scoliosis in pinealectomized chicken was about 50% although non-scoliotic pinealectomized chicken showed a similar BMD than the controls (sham or intact chicken). In FIG. 11, the chickens were exhibiting a scoliosis 7-days post-pinealectomy, while in FIG. 12, they were exhibiting a scoliosis 21-days post-pinealectomy. Treatment with melatonin, 3 mg/kg/day ip, increased BMD in treated animals. Treatment with melatonin, 3 mg/kg/day ip, increased BMD in treated animals.

Histological analysis indicated that decreased BMD occurred particularly at the cortical bone level (not shown).

Figure 13:
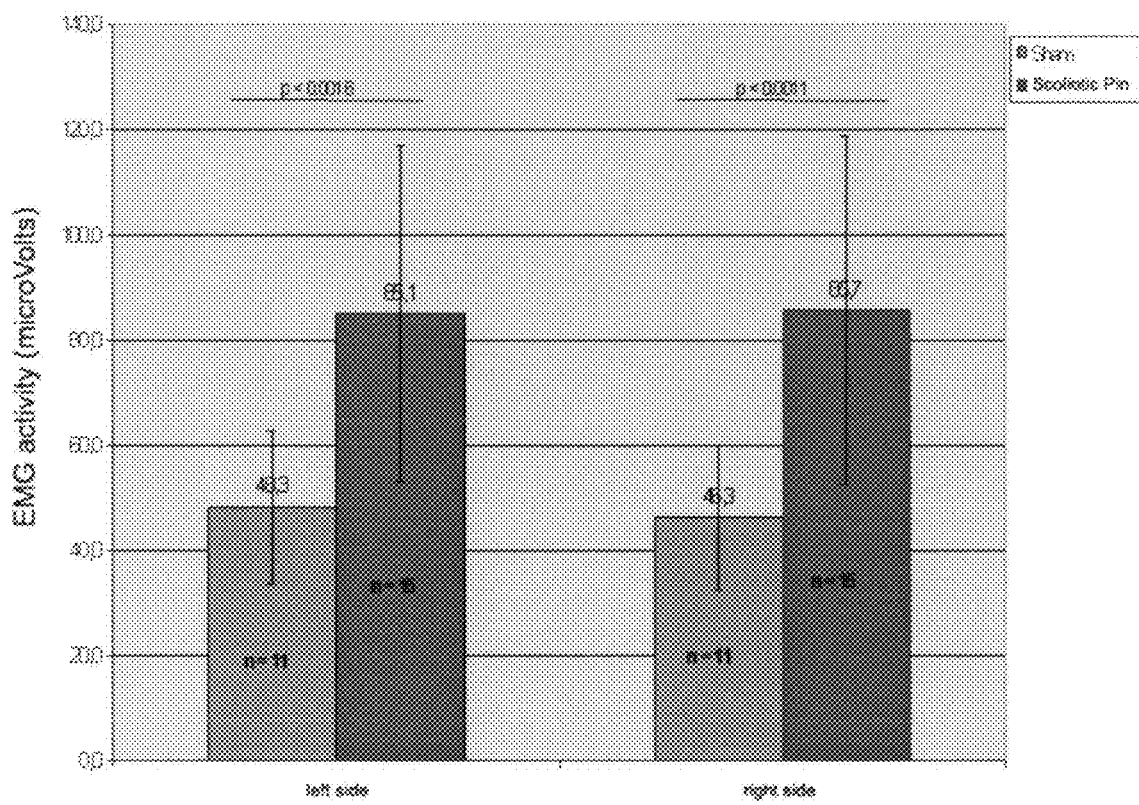
FIG. 13 graphically shows EMG activity in paraspinal musculature of pinealectomized chicken.

Interestingly, EMG measurement of paraspinal musculature activity using intramuscular electrodes revealed a 75% bi-lateral increase in muscular tone in scoliotic pinealectomized chicken at rest when compared to sham or non-scoliotic pinealectomized groups (FIG. 13). EMG analysis was performed with implanted electrodes 21-days post-pinealectomy. EMG activities were recorded in active chicken and compared between sham and scoliotic pinealectomized chicken. Determination of EMG activity at rest in paraspinal musculature of pinealectomized chicken.

Figure 14:
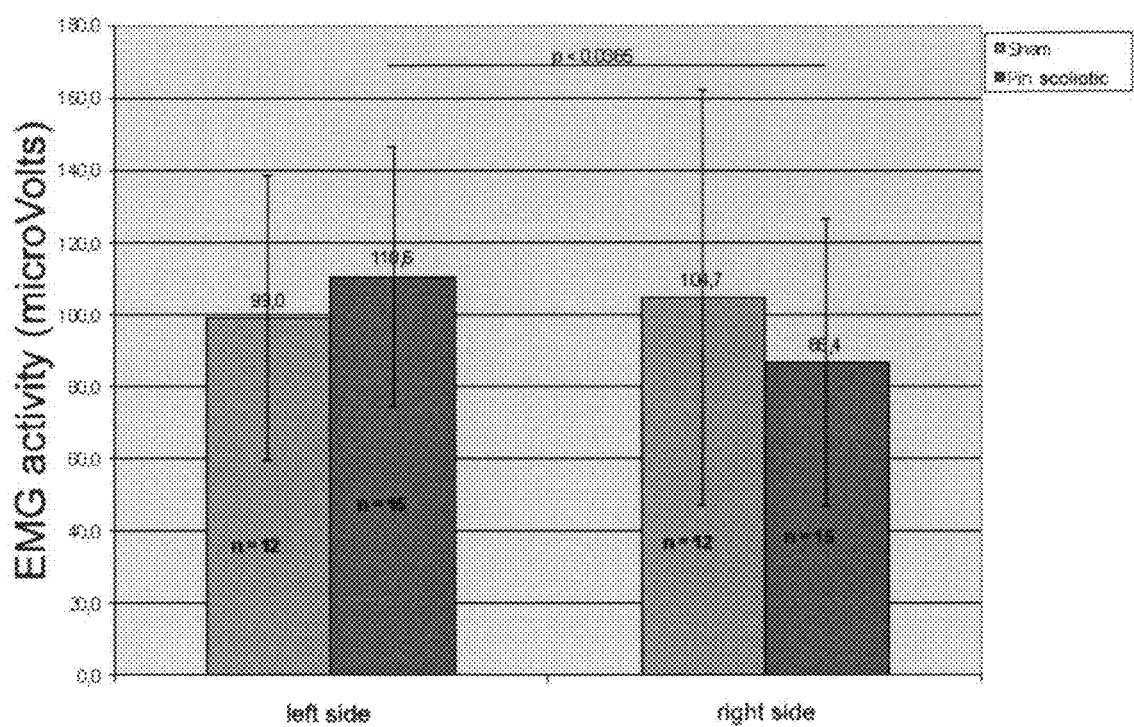
FIG. 14 graphically shows EMG activity in paraspinal musculature of pinealectomized chicken in movement.

Similar EMG analysis in active chicken showed an asymmetrical activity increased by 30% on the left side of paraspinal musculature of scoliotic chicken, corresponding to the spine deformation curve (left sided in 99% of scoliotic chicken, FIG. 14). No such effect was observed with non-scoliotic chicken.

Although the present invention has been described hereinabove by way of preferred embodiments thereof, it can be modified without departing from the spirit and nature of the subject invention as defined in the appended claims.

REFERENCES (1) Connor J M, Conner A N, Connor R A, Tolmie J L, Yeung B, Goudie D. Genetic aspects of early childhood scoliosis. Am J Med Genet 1987; 27(2):419-424.
(2) Machida M. Cause of idiopathic scoliosis. Spine 1999; 24(24):2576-2583.
(3) Axenovich T I, Zaidman A M, Zorkoltseva I V, Tregubova I L, Borodin P M. Segregation analysis of idiopathic scoliosis: demonstration of a major gene effect. Am J Med Genet 1999; 86(4):389-394.
(4) Wise C A, Barnes R, Gillum J, Herring J A, Bowcock A M, Lovett M. Localization of susceptibility to familial idiopathic scoliosis. Spine 2000; 25(18):2372-2380.
(5) Blank R D, Raggio C L, Giampietro P F, Camacho N P. A genomic approach to scoliosis pathogenesis. Lupus 1999; 8(5):356-360.
(6) Giampietro P F, Raggio C L, Blank R D. Synteny-defined candidate genes for congenital and idiopathic scoliosis. Am J Med Genet 1999; 83(3):164-177.
(7) Machida M, Murai I, Miyashita Y, Dubousset J, Yamada T, Kimura J. Pathogenesis of idiopathic scoliosis. Experimental study in rats. Spine 1999; 24(19):1985-1989.
(8) Wang X, Moreau M, Raso V J, Zhao J, Jiang H, Mahood J et al. Changes in serum melatonin levels in response to pinealectomy in the chicken and its correlation with development of scoliosis. Spine 1998; 23(22):2377-2381.
(9) McCarrey J R, Abbott U K, Benson D R, Riggins R S. Genetics of scoliosis in chickens. J Hered 1981; 72(1):6-10.
(10) Muccielli M L, Martinez S, Pattyn A, Goridis C, Brunet J F. Otlx2, an Otx-related homeobox gene expressed in the pituitary gland and in a restricted pattern in the forebrain. Mol Cell Neurosci 1996; 8(4):258-271.
(11) Bagnall K, Raso V J, Moreau M, Mahood J, Wang X, Zhao J. The effects of melatonin therapy on the development of scoliosis after pinealectomy in the chicken. J Bone Joint Surg Am 1999; 81(2):191-199.
(12) Bagnall K M, Raso V J, Hill D L, Moreau M, Mahood J K, Jiang H et al. Melatonin levels in idiopathic scoliosis. Diurnal and nocturnal serum melatonin levels in girls with adolescent idiopathic scoliosis. Spine 1996; 21(17):1974-1978.
(13) Sadat-Ali M, al Habdan I, al Othman A. Adolescent idiopathic scoliosis. Is low melatonin a cause? Joint Bone Spine 2000; 67(1):62-64.
(14) Brodner W, Krepler P, Nicolakis M, Langer M, Kaider A, Lack W et al. Melatonin and adolescent idiopathic scoliosis. J Bone Joint Surg Br 2000; 82(3):399-403.
(15) Borjigin J, Li X, Snyder S H. The pineal gland and melatonin: molecular and pharmacologic regulation. Annu Rev Pharmacol Toxicol 1999; 39:53-65.
(16) Jockers R, Petit L, Brydon L, de Coppet P, Strosberg A D. [Structure and function of melatonin receptors]. C R Seances Soc Biol Fil 1998; 192(4):659-667.
(17) Cardinali D P, Golombek D A, Rosenstein R E, Cutrera R A, Esquifino A I. Melatonin site and mechanism of action: single or multiple? J Pineal Res 1997; 23(1):32-39.
(18) Roka F, Brydon L, Waldhoer M, Strosberg A D, Freissmuth M, Jockers R et al. Tight association of the human Mel(1a)-melatonin receptor and G(i): precoupling and constitutive activity. Mol Pharmacol 1999; 56(5):1014-1024.
(19) Tintut Y, Parhami F, Le V, Karsenty G, Demer L L. Inhibition of osteoblast-specific transcription factor Cbfa1 by the cAMP pathway in osteoblastic cells. Ubiquitin/proteasome-dependent regulation. J Biol Chem 1999; 274(41):28875-28879.
(20) Nakade O, Koyama H, Ariji H, Yajima A, Kaku T. Melatonin stimulates proliferation and type I collagen synthesis in human bone cells in vitro. J Pineal Res 1999; 27(2):106-110.
(21) Roth J A, Kim B G, Lin W L, Cho M I. Melatonin promotes osteoblast differentiation and bone formation. J Biol Chem 1999; 274(31):22041-22047.
(22) Hyatt B A, Lohr J L, Yost H J. Initiation of vertebrate left-right axis formation by maternal Vg1. Nature 1996; 384(6604):62-65.
(23) von Gall C, Lewy A, Schomerus C, Vivien-Roels B, Pevet P, Korf H W et al. Transcription factor dynamics and neuroendocrine signaling in the mouse pineal gland: a comparative analysis of melatonin-deficient C57BL mice and melatonin-proficient C3H mice. Eur J Neurosci 2000; 12(3):964-972.
(24) Kaziro Y, Itoh H, Kozasa T, Nakafuku M, Satoh T. Structure and function of signal-transducing GTP-binding proteins. Annu Rev Biochem 1991; 60:349-400.
(25) Cowburn R F, O'Neill C, Ravid R, Winblad B, Fowler C J. Preservation of Gi-protein inhibited adenylyl cyclase activity in the brains of patients with Alzheimer's disease. Neurosci Lett 1992; 141(1):16-20.
(26) Feldman R D. Insulin-mediated sensitization of adenylyl cyclase activation. Br J Pharmacol 1993; 110(4):1640-1647.
(27) Cheng J C, Guo X, Sher A H. Persistent osteopenia in adolescent idiopathic scoliosis. A longitudinal follow up study [see comments]. Spine 1999; 24(12):1218-1222.

(28) Hans D, Biot B, Schott A M, Meunier P J. No diffuse osteoporosis in lumbar scoliosis but lower femoral bone density on the convexity. Bone 1996; 18(1):15-17.

(29) Courtois I, Collet P, Mouilleseaux B, Alexandre C. Bone mineral density at the femur and lumbar spine in a population of young women treated for scoliosis in adolescence. Rev Rhum Engl Ed 1999; 66(12):705-710.

(30) Cheng J C, Tang S P, Guo X, Chan C W, Qin L. Osteopenia in adolescent idiopathic scoliosis: a histomorphometric study. Spine 2001; 26(3):E19-E23.

(31) Papaioannou S, Tumber A M, Meikle M C, McDonald F. G-protein signaling pathways and oestrogen: a role of balanced maintenance in osteoblasts. Biochim Biophys Acta 1999; 1449(3): 284-292.

What is claimed is:

1. A method of classifying a human subject having adolescent idiopathic scoliosis (AIS) comprising: providing a cell sample isolated from the subject; detecting an impairment in melatonin-signaling pathway in the sample in the presence and in the absence of a known melatonin-signaling pathway agonist, wherein the impairment is detected by an accumulation of cyclic adenosine 5'-monophosphate (cAMP) in the cell sample as compared to that in a control cell sample whereby the results of the detecting step enables the classification of the subject having AIS in one AIS subgroup.

2. The method of claim 1, further comprising a step of selecting a treatment for the subject based on the results of the detecting step.

3. The method of claim 1, wherein said accumulation of cAMP is induced by a known activator of adenylyl cyclase, and wherein the impairment is detected by an inhibition of said accumulation by a known melatonin-signaling pathway agonist that is detectably reduced in the cell sample as compared to that obtained in a control cell.

4. The method of claim 3, wherein said known activator of adenylyl cyclase is forskolin.

5. The method of claim 3, wherein said known melatonin-signaling pathway agonist is melatonin.

6. The method of claim 1, wherein said known melatonin-signaling pathway agonist is GTP.

7. The method of claim 1, wherein said cells are selected from the group consisting of osteoblasts, osteoclasts, lymphocytes, monocytes and myoblasts.

8. The method of claim 1, wherein said cells are blood cells.

9. The method of claim 1, wherein said cells are lymphocytes.

* * * * *